(12) United States Patent
Steinmetz et al.

(10) Patent No.: US 11,730,833 B2
(45) Date of Patent: *Aug. 22, 2023

(54) COATED PLANT VIRUS IMAGING AGENTS

(71) Applicant: CASE WESTERN RESERVE UNIVERSITY, Cleveland, OH (US)

(72) Inventors: Nicole F. Steinmetz, San Diego, CA (US); Michael Bruckman, Cleveland, OH (US); Lauren Randolph, State College, PA (US)

(73) Assignee: CASE WESTERN UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/522,182

(22) Filed: Nov. 9, 2021

(65) Prior Publication Data

US 2022/0211881 A1 Jul. 7, 2022

Related U.S. Application Data

(63) Continuation of application No. 16/279,482, filed on Feb. 19, 2019, now Pat. No. 11,167,047, which is a continuation of application No. 15/937,681, filed on Mar. 27, 2018, now Pat. No. 10,207,014, which is a continuation of application No. 14/818,812, filed on Aug. 5, 2015, now Pat. No. 9,925,281.

(60) Provisional application No. 62/033,297, filed on Aug. 5, 2014.

(51) Int. Cl.
*A61K 49/18* (2006.01)
*A61K 49/10* (2006.01)
*A61K 49/08* (2006.01)

(52) U.S. Cl.
CPC ........ *A61K 49/1896* (2013.01); *A61K 49/085* (2013.01); *A61K 49/108* (2013.01)

(58) Field of Classification Search
None
See application file for complete search history.

(56) References Cited

U.S. PATENT DOCUMENTS

| | | | |
|---|---|---|---|
| 5,004,606 A | 4/1991 | Frincke | |
| 9,925,281 B2* | 3/2018 | Steinmetz | ............ A61K 49/108 |
| 10,086,095 B2* | 10/2018 | Steinmetz | .......... A61K 49/1896 |
| 10,207,014 B2* | 2/2019 | Steinmetz | .......... A61K 49/1896 |
| 10,478,510 B2 | 11/2019 | Steinmetz | |
| 11,020,497 B2* | 6/2021 | Steinmetz | .......... A61K 49/1884 |
| 11,167,047 B2* | 11/2021 | Steinmetz | ............ A61K 49/085 |
| 11,253,610 B2 | 2/2022 | Steinmetz | |
| 2005/0019270 A1 | 1/2005 | Finlay et al. | |
| 2007/0248617 A1 | 10/2007 | Bachmann et al. | |
| 2007/0258889 A1 | 11/2007 | Douglas et al. | |
| 2007/0284545 A1 | 12/2007 | Isacsson et al. | |
| 2010/0183504 A1* | 7/2010 | Chen | .................. A61K 41/0071 424/9.34 |
| 2015/0033418 A1 | 1/2015 | Lommel et al. | |
| 2015/0265696 A1 | 9/2015 | Gourapura et al. | |
| 2020/0179468 A1 | 6/2020 | Steinmetz | |
| 2022/0211881 A1* | 7/2022 | Steinmetz | ............ A61K 49/108 |

FOREIGN PATENT DOCUMENTS

| | | |
|---|---|---|
| JP | 2009524699 A | 7/2009 |
| WO | 01/18199 A1 | 3/2001 |
| WO | 2001/0026682 A2 | 4/2001 |
| WO | 2003092623 A2 | 11/2003 |
| WO | 2012078069 A1 | 6/2012 |
| WO | 2013181557 A1 | 12/2013 |
| WO | 2014059021 A1 | 4/2014 |
| WO | 2015/039255 A1 | 3/2015 |
| WO | 2015/188110 A1 | 12/2015 |
| WO | 2016019393 A1 | 2/2016 |
| WO | 2016073972 A1 | 5/2016 |
| WO | 2016/149264 A1 | 9/2016 |
| WO | 2017/004123 A1 | 1/2017 |

OTHER PUBLICATIONS

Xiao et al. (International Journal of Molecular Medicine. 2016; 38: 1319-326).*
Zhang et al. (Theranostics. 2018; 8 (9): 2521-2548).*
Pellico et al. (Contrast Media and Molecular Imaging. 2019; Article ID 1845637: 1-13).*
Bruckman et al. (Nano Letters. Mar. 2014; 14: 1551-1558).*
Royston et al. (Journal of Colloidal and Interface Science. 2009; 332: 402-407).*

(Continued)

*Primary Examiner* — Shanon A. Foley
(74) *Attorney, Agent, or Firm* — Tarolli, Sundheim, Covell & Tummino, LLP

(57) ABSTRACT

An imaging nanoparticle comprising a plant virus particle having an interior surface and an exterior surface, an imaging agent that is linked to the interior and/or exterior surface, and a layer of biocompatible mineral such as silica coated over the exterior surface, is described. The imaging nanoparticle can be used in method of generating an image of a tissue region of a subject, by administering to the subject a diagnostically effective amount of an imaging nanoparticle and generating an image of the tissue region of the subject to which the imaging nanoparticle has been distributed.

13 Claims, 10 Drawing Sheets

(56) References Cited

OTHER PUBLICATIONS

Agrawal Arpita et al: "Differential Uptake of Chemically Modified Cowpea Mosaic Virus Nanoparticles in Macrophage Subpopulations Present in Inflammatory and Tumor Microenvironments", Biomacromolecules, vol. 13, No. 10, Oct. 2012 pp. 3320-3326, XP002780313.
Applicant Case Western Reserve University; "Cancer Immunotherapy Using Virus Particles"; European Patent Application No. 21201960.8; Extended European Search Report dated Jan. 19, 2022; 11 pgs.
Brennan Frank R et al: "Cowpea mosaic virus as a vaccine carrier of heterologous antigens", Molecular Biotechnology, vol. 17, No. 1, Jan. 2001 (Jan. 2001), pp. 15-26, XP002780312, ISSN: 1073-6085.
Gonzalez Maria Jet Al: "Interaction of Cowpea Mosaic Virus (CPMV) Nanoparticles with Antigen Presenting Cells In Vitro and In Vivo", PLOS ONE, vol. 4, No. 11, Nov. 2009 (Nov. 2009), XP002780311, ISSN: 1932-6203.
Patrick h. lizotte: "Novel approaches to targeting innate immunity for cancer immunotherapy", Proquest Dissertations Publishing, May 2015 (May 2015), XP002780316, Retrieved from the Internet: URL:https://search.proquest.com/docview/1695832154?pq-origsite=gscholar [retrieved on Apr. 19, 2018].
Saunders Ket Al: "Efficient generation of cowpea mosaicvirus empty virus-like particles by the proteolytic processing of precursors in insect cells and plants", Virology, Elsevier, Amsterdam, NL, vol. 393, No. 2, Oct. 25, 2009 (Oct. 25, 2009), pp. 329-337, XP026691170, ISSN: 0042-6822, DOI: 10.1016/J.VIROL.2009.08.023 [retrieved on Sep. 5, 2009].
"CWRU researcher to turn plant virus shells against human cancers", The Daily, CWRU Researcher to Turn Plant Virus Shells Against Human Cancers. Case Western Reserve University, Apr. 18, 2016.
Alaa A. AL. Aljabali, et al.; "CPMV-DOX Delivers", Molecular Pharmaceutics, vol. 10, No. 1, Jan. 7, 2013, pp. 3-10, XP055347068, US ISSN: 1543-8384, DOI: 10.1021/MP3002057.
Applicant: Case Western Reserve University; "Cancer Immunotherapy Using Virus Particles"; Canadian Office Action, dated Aug. 4, 2020; 3 pgs.
Applicant: Case Western Reserve University; "Cancer Immunotherapy Using Virus Particles"; European Patent Application No. 18764856.3 for Supplementary European Search Report dated Dec. 22, 2020; 8 pgs.
Applicant: Case Western Reserve University; "Plant Virus Particles for Delivery of Antimitotic Agents"; Extended European Search Report; dated Aug. 25, 2020; 11 pgs.
Canan Uluog, et al.: "Intermediate dose of methotrexate toxicity in non-Hodgkin lymphoma", General Pharmacology, vol. 32, 1999, pp. 215-218, XP55711259.
Chariou, et al., "Detection and Imaging of Aggressive Cancer Cells Using an Epidermal Growth Factor Receptor (EGFR)-Targeted Filamentous Plant Virus-Based Nanoparticle", Bioconjug Chem. Feb. 18, 2015; 26(2): 262-269.
European Search Report for Patent Application No. 15857504.3-1111/3215520, dated May 7, 2018.
Francisco, Joseph A., et al.; "cAC10-vcMMAE, an anti-CD30-monomethyl auristatin E conjugate with potent and selective antitumor activity", Blood, American Society of Hematology, US, vol. 102, No. 4, Aug. 15, 2003, pp. 1458-1465, XP002738948, ISSN: 0006-4971, DOI: 10.1182/BLOOD-2003-01-0039.
International Search Report for Application No. PCT/US15/59675 (dated 2016).
Inventor: Nicole Steinmetz, "Rod-Shaped Plant Virus Nanoparticles as Imaging Agent Platforms"; U.S. Appl. No. 16/149,828, filed Oct. 2, 2018, Office Action dated Aug. 28, 2020, 22 pgs.
Jantipa Jobsri, et al.: Plant Virus Particles Carrying Tumour Antigen Activate TLR7 and Induce High Levels of Protective Antibody, Plos One, vol. 10, No. 2, Jan. 1, 2015, pp. 1-16, XP055347065, DOI: 10.1371/journal.pone.0118096.
Lee, K. L., et al.; "Combination of Plant Virus Nanoparticle-Based in Situ Vaccination with Chemotherapy Potentiates Antitumor Response". Nano letters, 17(7); Epub Jun. 26, 2017; 4019-4028. https://doi.org/10.1021/acs.nanolett.7b00107.
Lizotte, et al., "Plant-derived viral-like nanoparticle immunotherapy suppress development of metastatic lung cancer", Journal of Immunology, vol. 194, Issue 1 Supplement, May 2015; 4 pgs.
Matsuura et al. Self-assembly of Ni-NT A-modified [3-annulus peptides into artificial viral capsids and encapsulation of His-tagged proteins. Org. Biomol. Chem., 2016, 14, 7869. DOI: 10.1039/c6ob01227b (Year: 2016).
Miermont et al., "Cowpea Mosaic Virus Capsid: A promising Carrier for the Development of Carbohydrate Based Antitumor Vaccines", Chem. Eur. J., 2008, vol. 14, pp. 4939-4947.
Nicole F.Steinmetz, et al.; "Coated Plant Virus Imaging Agents"; U.S. Appl. No. 16/279,482, filed Feb. 19, 2019; Non-Final Rejection dated Mar. 23, 2021; 91 pgs.
Nicole F.Steinmetz; "Viral Nanoparticle Multimers"; U.S. Appl. No. 14/761,444, filed Jul. 16, 2015; Final Office Action dated Mar. 11, 2021; 11 pgs.
Office action for Chinese Patent Application No. 201580063662.6, dated Mar. 4, 2020.
Office action for European Patent Application No. 15 857 504.3-1111, dated Mar. 18, 2020.
Office action for Japanese Patent Application No. 2017-524349, drafted Jan. 31, 2020; dated Feb. 10, 2020; 6 pgs.
Pfizer Ltd.: "Package leaflet: Information for the patient", Jan. 1, 2014, XP55565400, Walton Oaks, Tadworth, Surrey, UK Retrieved from the Internet: URL:https://www.medicines.org.uk/emc/files/pil.6184.pdf [retrieved on Mar. 6, 2019].
Plchova et al. Expression of Human papillomavirus 16 E7ggg oncoprotein on N- and C-terminus of Potato virus X coat protein in bacterial and plant cells. Protein Expression and Purification 77 (2011); p. 146-152.
Sheen et al., "Stimulating Antitumor Immunity with Nanoparticles", Wiley Interdiscip Rev Nanomed Nanobiotechnol, Oct. 2014, vol. 6, pp. 496-505.
Smyth etal. Treatment of rapidly growing K-BALB and CT26 mouse tumours using Semliki Forest virus and its derived vector. Gene Therapy (2005) 12, 147-159.
Sourabh Shukla, et al.: "The Impact of Aspect Ratio on the Biodistribution and Tumor Homing of Rigid Soft-Matter Nanorods", Advanced Healthcare Materials, vol. 4, No. 6, Apr. 1, 2015, pp. 874-882, XP055473103, DE ISSN: 2192-2640, DOI: 10.1002/adhm.201400641.
Trevor W. E. Robinson, et al., "The Journal of Investigative Dermatology the Effect of Methotrexate on Cell Division in the Epidermis of the Young Rat"; The Journal of investigative Dermatology, vol. 53, 1969, pp. 223-227, XP55711263.
Wen et al. Design of virus-based nanomaterials for medicine, biotechnology, and energy. Chem. Soc. Rev., 2016, 45, 4074. DOI: 10.1039/c5cs00287g (Year: 2016).
Yildiz, et al., "Applications of viral nanoparticles in medicine", Current Opinion in Biotechnology, vol. 22, Issue 6, (2011); pp. 901-908.
Lee et al. "Biodegradable Viral Nanoparticle/Polymer Implants Prepared via Melt-Processing", ACS Nano ePub Sep. 13, 2017 vol. 11 No. 9 pp. 8777-8780.
Lee et al., "PEGylation to Improve Protein Stability During Melt Processing", Macromol Biosci 1-43, 57-75, Oct. 2015 vol. 15 No. 10 pp. 1332-1337.
Nicole F. Steinmetz; U.S. Appl. No. 16/347,503, filed May 3, 2019; NonFinal Rejection dated Jun. 15, 2022; 36 pgs.
Nicole F. Steinmetz; U.S. Appl. No. 16/614,676, filed Nov. 18, 2019; NonFinal Rejection dated Jun. 3, 2022; 28 pgs.
Czapar, Anna et al. Tobacco Mosaic Virus Delivery of Phenanthriplatin for Cancer therapy. American Chemical Society. Nano 2016 (10) pp. 4119-4126 (Year: 2016).
Le, Duc et al. Biodistribution of Filamentous Plant Virus Nanoparticles: Pepino Mosaic Virus versus Potato Virus X. Biomacromolecules 219 Jan. 14; 20(a): pp. 469-477. (Year 2019).

(56) References Cited

OTHER PUBLICATIONS

Le, Duc et al. Chemical addressability of potoato virus X for its applications in bio/nanotechnology. El Sevier. Journal of Structural Biology 200 (2017). pp. 360-368. (Year: 2017).

Le, Duc et al. Potato virus X, a filamentous plant viral nanoparticle for doxorubicin delivery in cancer therapy. Royal Society of Chemistry. Nanoscale, 2017 (9). pp. 2348-2357. (Year 2017).

Nicole F. Steinmetz, U.S. Appl. No. 16/998,210, filed Aug. 7, 2020; Non-Final OA dated Dec. 7, 2022.

Tran, Hong Hanh. Developing a plant virus-based expression system for the expression of vaccines against Porcine Reproductive and Respiratory Syndrome Virus. Western Graduate & Postdoctoral Studies. Electronic Thesis and Dissertation Repository. (Year: 2017).

Imamura et al. ("FOXA 1 promotes tumor progression in prostate cancer via the insulin-like growth factor binding protein 3 pathway." (2012)).

Lam, et al. (WIREs Nanomed Nanobiotechnol Jan./Feb. 2018 vol. 10: 1-18).

Mitoxantrone. Drug Bank Online. Website. https://go.drugbank.com/drugs/DB01204. (Accessed Dec. 15, 2022) (Year: 2022).

Mosquera et al. (Acc. Chem. Res. 2018, 51, 9, 2305-2313 Publication Date: Aug. 29, 2018.

Nicole F.Steinmetz; U.S. Appl. No. 16/597,509, filed Oct. 9, 2019; Non-Final Office Action, dated Dec. 27, 2022; 12 pgs.

Nicole F.Steinmetz; U.S. Appl. No. 16/759,652, filed Apr. 27, 2020; Final Office Action, dated Dec. 12, 2022; 15 pgs.

Nicole F.Steinmetz; U.S. Appl. No. 17/129,463, filed Dec. 21, 2020; Non-Final Office Action, dated Dec. 8, 2022; 32 pgs.

Nicole F.Steinmetz; U.S. Appl. No. 17/677,147, filed Feb. 22, 2022; Non-Final Office Action, dated Jan. 13, 2023; 22 pgs.

Pretto et al. ("Versatile reversible cross-linking strategy to stabilize CCMV virus like particles for efficient siRNA delivery." Bioconjugate chemistry 30.12 (2019): 3069-3077).

Tamoxifen. Drug Bank Online. Website. https://go.drugbank.com/drugs/DB00675. (Accessed: Dec. 15, 2022) (Year: 2022).

Temming et al. (bioconjugate Chemistry. 2006; 17: 1385-1394).

* cited by examiner

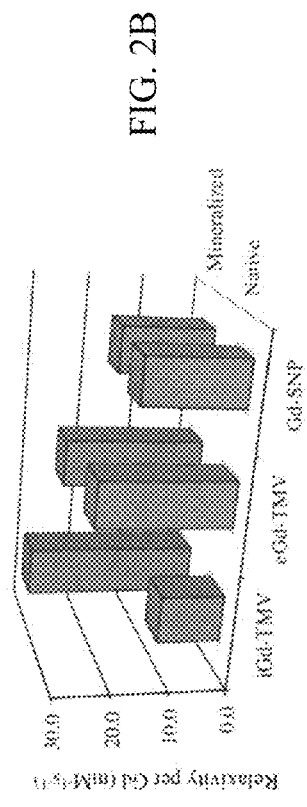
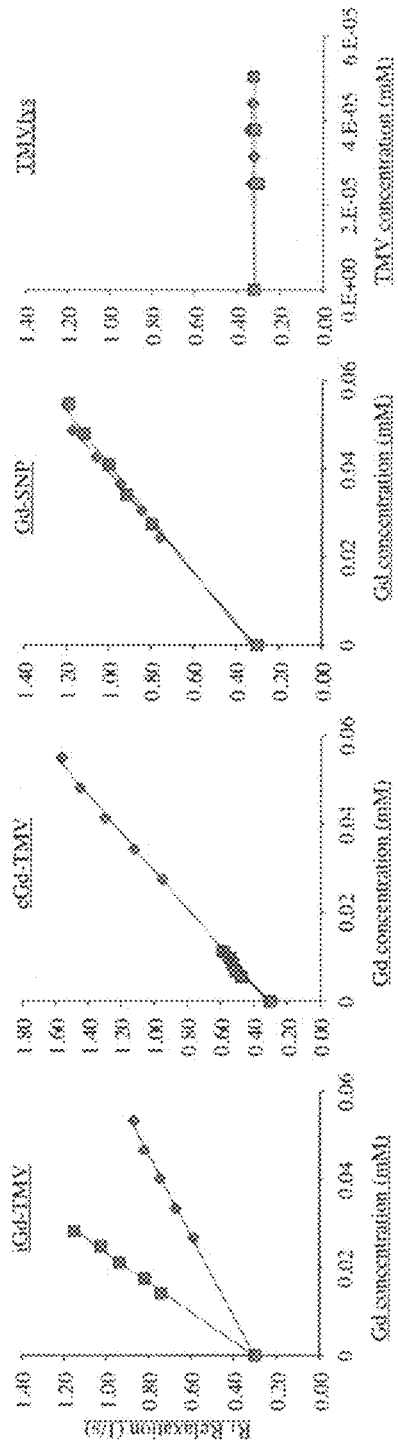
FIG. 2A FIG. 2B FIG. 2C FIG. 2D FIG. 2E FIG. 2F

FIG. 4A
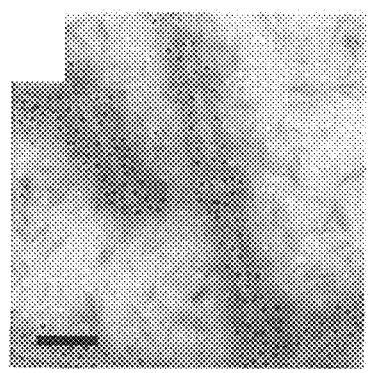
FIG. 4B
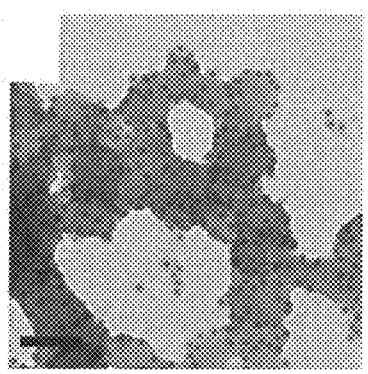
FIG. 4C
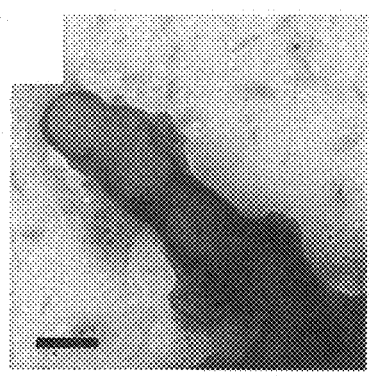
FIG. 4D
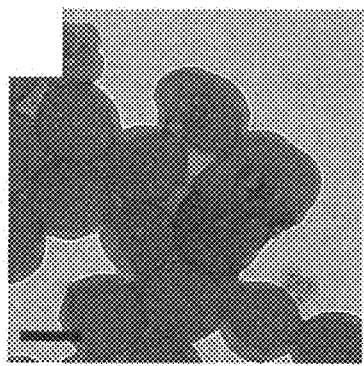
FIG. 4E
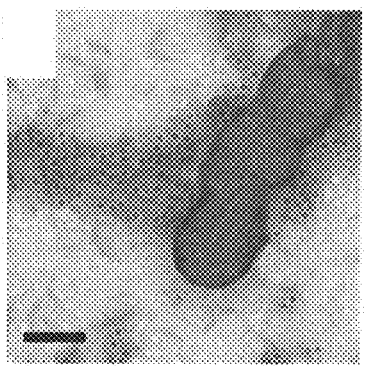
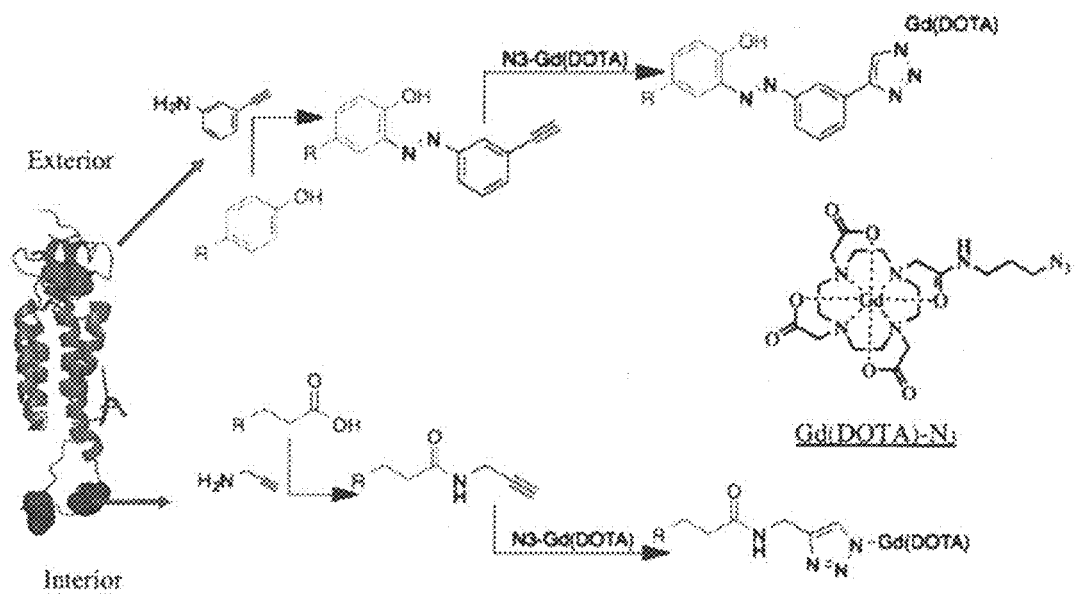
Fig. 5

COATED PLANT VIRUS IMAGING AGENTS

CROSS-REFERENCE TO RELATED APPLICATIONS

This application claims priority to U.S. Provisional Patent Application Ser. No. 62/033,297, filed Aug. 5, 2014, which is incorporated herein by reference

GOVERNMENT FUNDING

The present invention was supported by a grant from the National Science Foundation (CMMI NM 1333651) and the National Institutes of Health (NIH R21HL121130). The Government has certain rights in this invention.

BACKGROUND

Molecular imaging facilitates the early detection of disease, allows risk stratification, disease monitoring, longitudinal imaging and treatment follow up. A variety of imaging modalities have been developed, including positron electron tomography (PET), computed tomography (CT), and magnetic resonance imaging (MRI). The latter is gaining popularity because of its excellent soft tissue contrast, spatial resolution and penetration depth, and because the non-ionizing radiation is safer for repeated imaging sessions. However, MRI has a low sensitivity to contrast-enhancement agents, which provide important information about molecular features in vivo. Nanoparticles are ideal platforms for the development of better contrast-enhancement agents because they can carry large payloads, they can be modified with targeting ligands to confer molecular specificity and their structure enhances ionic relaxivity.

Several nanoparticle-based MRI contrast agents have been described, including nanoemulsions, dendrimers, silica and gold nanoparticles, and viral nanoparticles (VNPs). Bruckman et al., Nanotechnology. 2013; 24(46):462001. Nanoparticles increase the longitudinal relaxivity (positive contrast, $R_1$) by reducing the molecular tumbling rate ($\tau_R$) of chelated paramagnetic ions such as Gd following surface conjugation. Caravan et al., 2009; 4(2):89-100. In theory, free chelated Gd ions with a relaxivity of ~5 mM$^{-1}$ s$^{-1}$ can achieve relaxivities of up to 80 mM$^{-1}$ s$^{-1}$ at 1.5 T, the common mode of MRI used in the clinic. This is based on the optimization of properties such as particle stiffness, bulk water accessibility and the chelating molecule, although experimentally it remains challenging to achieve such high values.

The inventors have focused the development of VNPs for medical applications because the manufacture of such proteinaceous nanoparticles in a variety of shapes and sizes is highly reproducible and scalable, and the particles themselves are amenable to functionalization using synthetic biology, genetic engineering and bioconjugation chemistry. Van Kan-Davelaar et al., British Journal of Pharmacology. 2014; 171(17):4001-4009. Several VNP-based MRI contrast agents have been described, including the icosahedral plant viruses Cowpea mosaic virus (CPMV) (Prasuhn et al., Chemical Communications. 2007(12):1269), Cowpea chlorotic mottle virus (CCMV) (Liepold et al., Magnetic Resonance in Medicine. 2007; 58(5):871-9), bacteriophages P22, MS2 and Qβ, and the plant virus Tobacco mosaic virus (TMV), which naturally occurs as rods but can also be produced as spheres. Bruckman et al., Journal of Materials Chemistry B. 2013; 1(10):1482A.

A few recent articles discuss the in vivo performance of these protein-based MRI contrast agents. Min et al., Biomacromolecules. 2013; 14(7):2332-9. For example, the inventors recently showed that TMV particles can be employed to image the molecular features of atherosclerotic plaques using a vascular cell adhesion molecule (VCAM-1)-targeted Gd(DOTA)-loaded probe. Bruckman et al., Nano Letters. 2014; 14(3):1551-8. The $T_1$ relaxivity of this nanoparticle was ~15 mM$^{-1}$ s$^1$, yielding a per particle relaxivity of 35,000 mM$^{-1}$ s$^1$ at 60 MHz, thus allowing the imaging of molecular features in vivo at submicromolar doses of Gd(DOTA). However, there remains a need for imaging agents with improved performance, such as increased sensitivity and decreased immunogenicity.

SUMMARY

The inventors have investigated the materials and biological properties of TMV-based MRI contrast agents, specifically to develop probes for macrophage imaging. The active or passive targeting of immune cells is a useful strategy to investigate the cellular components involved in disease progression associated with inflammation. Macrophage imaging was studied as a function of contrast agent shape and surface coating. Protein-based nanoparticles (TMV rods and TMV spheres) were mineralized with silica coatings.

The inventors chose silica as a coating material because it is biologically inert and coating techniques are well established. Tarn et al., Accounts of Chemical Research. 2013: 46(3):792-801. For example, silica mineralization has been used to improve the biocompatibility of nanoparticles based on gold (Lee et al., Toxicology Letters. 2012; 209(1):51-7), iron oxide (Singh et al., Journal of Biomedical Materials Research Part A. 2012; 100A(7):1734-42) and quantum dots (Durgadas et al., Biomaterials. 2012; 33(27):6420-9). The inventors hypothesized that the silica coating would maintain high relaxivities, while providing a means for antibody evasion. Research indicates that TMV-specific antibodies are prevalent in the population due to presence of TMV in food and cigarettes. Liu et al., PLoS ONE. 2013; 8(4): e60621. The silica shell was therefore investigated to see if it would protect TMV and SNP from recognition by TMV-specific antibodies. This is an important goal for potential clinical application to prevent premature clearance of the contrast agent and maintain stable and reproducible pharmacokinetics for repeated imaging sessions.

In one aspect, the present invention provides an imaging nanoparticle, comprising a plant virus particle having an interior surface and an exterior surface, an imaging agent that is linked to the interior and/or exterior surface, and a layer of biocompatible mineral coated over the exterior surface. In some embodiments, the biocompatible mineral is silica, with in further embodiments the plant virus is a rod-shaped virus particle.

Another aspect of the present invention provides a method of generating an image of a tissue region of a subject. The method includes administering to the subject a diagnostically effective amount of an imaging nanoparticle, comprising a plant virus particle having an interior surface and an exterior surface, an imaging agent that is linked to the interior and/or exterior surface, and a layer of biocompatible mineral coated over the exterior surface, and generating an image of the tissue region of the subject to which the imaging nanoparticle has been distributed. In some embodiments, the biocompatible mineral is silica, with in further embodiments the plant virus is a rod-shaped virus particle.

BRIEF DESCRIPTION OF THE FIGURES

The present invention may be more readily understood by reference to the following drawings.

FIG. 2 (A-F) provides a table (A) and accompanying (B) bar graph showing Gd loading per particle, relaxivity per Gd and per particle (in $mM^{-1}$ $s^{-1}$ at 60 MHz). The lower panels show relaxivity curves for (C) iGd-TMV, (D) eGd-TMV, (E) Gd-SNP, and (F) unmodified TMV. One curve is for pre-mineralized (native) particles, while the other curves are post-mineralized particles. TMVlys shows the relaxivity curves for unlabeled TMVlys at virus concentrations matching values for iGd-TMV curves. *Gd per SNP calculated based on their size/volume relationships.

FIG. 4 (A-E) provides images showing the Binding of gold-labeled anti-TMV antibodies to (A) TMV, (B) SNP, (C) Si-TMV, (D) Si-SNP, and (E) a mix of TMV and Si-TMV. Scale bars=100 nm.

FIG. 5 provides a schematic diagram showing the bioconjugation of TMV rods.

DETAILED DESCRIPTION

Figure 1A:
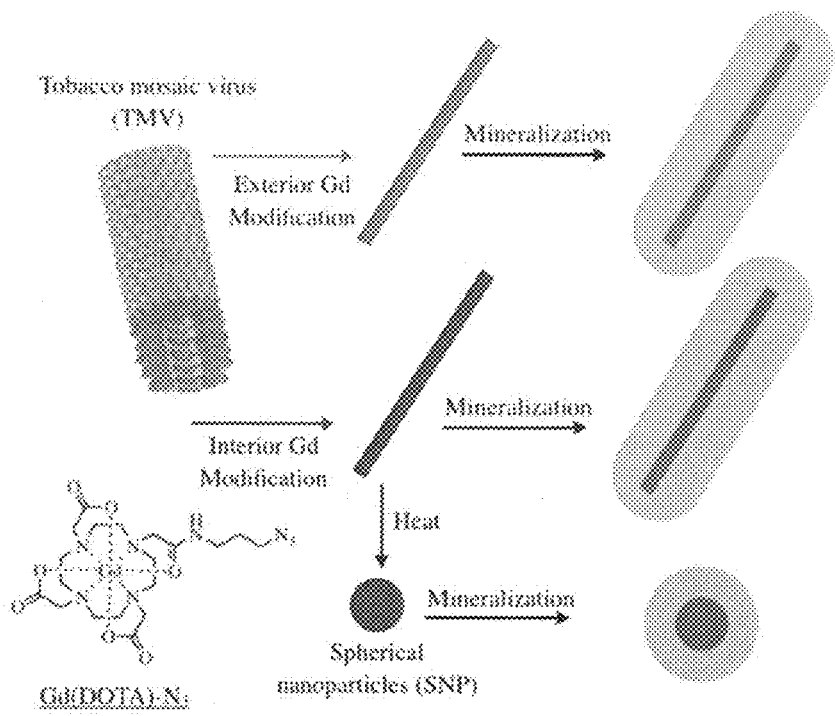
FIG. 1 (A, B) provides a A) the bioconjugation and mineralization scheme which produces Gd(DOTA)-loaded and silica-coated TMV rods and spheres; and B) TEM and SEM imaging of TMV-based contrast agents. Scale bars=100 nm (TEM, black) or 500 nm (SEM, white).

Imaging nanoparticles comprising a plant virus particle having an interior surface and an exterior surface, an imaging agent that is linked to the interior and/or exterior surface, and a layer of biocompatible mineral such as silica coated over the exterior surface are described. The imaging nanoparticles can be used in a method of generating an image of a tissue region of a subject such as a tumor or atherosclerotic tissue by administering the imaging nanoparticles to the subject and generating an image of the tissue region of the subject to which the imaging nanoparticles have distributed.

Definitions

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural references unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of ±20% or 110%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Image" or "imaging" refers to a procedure that produces a picture of an area of the body, for example, organs, bones, tissues, or blood.

A "subject," as used herein, can be any animal, and may also be referred to as the patient. Preferably the subject is a vertebrate animal, and more preferably the subject is a mammal, such as a domesticated farm animal (e.g., cow, horse, pig) or pet (e.g., dog, cat). In some embodiments, the subject is a human.

"Pharmaceutically acceptable" as used herein means that the compound or composition is suitable for administration to a subject for the methods described herein, without unduly deleterious side effects.

As used herein, the term "relaxation time" refers to the time required for a nucleus which has undergone a transition into a higher energy state to return to the energy state from which it was initially excited. Regarding bulk phenomena, the term "relaxation time" refers to the time required for a sample of nuclei, the Boltzmann distribution of which has been perturbed by the application of energy, to reestablish the Boltzmann distribution. The relaxation times are commonly denoted $T_1$ and $T_2$. $T_1$ is referred to as the longitudinal relaxation time and $T_2$ is referred to as the transverse relaxation time. As used herein, the term "relaxation time" refers to the above-described relaxation times either together or in the alternative. An exhaustive treatise on nuclear relaxation is available in Banci, L, et al. Nuclear and Electron Relaxation, VCH, Weinheim, 1991, which is herein incorporated by reference.

As used herein, the term "diagnostically effective amount" refers to an amount of contrast agent that is sufficient to enable imaging of the contrast agent in cells, tissues, or organisms using imaging equipment.

As used herein, a protein such as an antibody "specifically binds" when the antibody preferentially binds a target structure, or subunit thereof, but binds to a substantially lesser degree or does not bind to a biological molecule that is not a target structure. Antibodies that specifically bind to a target structure, or subunit thereof, do not cross-react with biological molecules that are outside the target structure family.

"Targeting," as used herein, refers to the ability of an imaging nanoparticle to be delivered to and preferentially accumulate in the target tissue in a subject.

"Biocompatible" as used herein, refers to any material that does not cause injury or death to the animal or induce an adverse reaction in an animal when placed in intimate contact with the animal's tissues. Adverse reactions include for example inflammation, infection, fibrotic tissue formation, cell death, or thrombosis. The terms "biocompatible" and "biocompatibility" when used herein are art-recognized and mean that the material is neither itself toxic to a subject, nor degrades (if it degrades) at a rate that produces byproducts (e.g., monomeric or oligomeric subunits or other byproducts) at toxic concentrations, does not cause prolonged inflammation or irritation, or does not induce more than a basal immune reaction in the host.

In one aspect, the present invention provides an imaging nanoparticle. The imaging nanoparticle comprises a plant virus particle having an interior surface and an exterior surface, an imaging agent that is linked to the interior and/or exterior surface, and a layer of biocompatible mineral coated over the exterior surface.

Plant Viruses

The imaging nanoparticles of the present invention are based on plant virus particles. Plant virus particles preferably grow in plants, and have the advantages of being readily cultivated, and are unlikely to cause infection when used in vivo in a subject. Plant virus particles are categorized based on their source and structure. In various embodiments, virus particles having an icosahedral, filamentous, or rod-shaped structure can be used. Preferably, the virus particles used are non-enveloped virus particles. Examples of icosahedral plant viruses include cowpea mosaic virus, brome mosaic virus, cowpea chlorotic mottle virus, etc. Use of filamentous or rod-shaped plant virus particles is preferred, in part as a result of the proclivity of these viral particles to be taken up by diseased tissue.

A filamentous plant virus is a virus that primarily infects plants and has a non-enveloped filamentous structure. A filamentous structure is a long, thin virion that has a filament-like or rod-like shape that is much longer than it is wide and therefore has a high-aspect ratio. For example, Alphaflexiviridae have a length of about 470 to about 800 nm, and a diameter of about 12-13 nm. Filament-like virus particles are flexible in addition to being long and thin, and therefore some embodiments of the invention are directed to use of a flexible filamentous plant virus. As described herein, use of filamentous plant viruses provides the advantages of improved tumor targeting and penetration. Embodiments of the invention can deliver about 10%, about 20%, about 30%, about 40%, or even about 50% or more of the injected dose to tumor tissue.

In some embodiments, the filamentous plant virus belongs to a specific virus family, genus, or species. For example, in some embodiments, the filamentous plant virus belongs to the Alphaflexiviridae family. The Alphaflexiviridae family includes the genus Allexivirus, Botrexvirus, Lolavirus, Mandarivirus, Potexvirus, and Sclerodamavirus. In some embodiments, the filamentous plant virus belongs to the genus Potexvirus. In further embodiments, the filamentous plant virus belongs to the Potato Virus X species.

In some embodiments, the imaging nanoparticle is based on a rod-shaped plant virus. A rod-shaped plant virus is a virus that primarily infects plants, is non-enveloped, and is shaped as a rigid helical rod with a helical symmetry. Rod shaped viruses also include a central canal. Rod-shaped plant virus particles are distinguished from filamentous plant virus particles as a result of being inflexible, shorter, and thicker in diameter. For example, Virgaviridae have a length of about 200 to about 400 nm, and a diameter of about 15-25 nm. Virgaviridae have other characteristics, such as having a single-stranded RNA positive sense genome with a 3'-tRNA like structure and no polyA tail, and coat proteins of 19-24 kilodaltons.

In some embodiments, the rod-shaped plant virus belongs to a specific virus family, genus, or species. For example, in some embodiments, the rod-shaped plant virus belongs to the Virgaviridae family. The Virgaviridae family includes the genus Furovirus, Hordevirus, Pecluvirus, Pomovirus, Tobamovirus, and Tobravirus. In some embodiments, the rod-shaped plant virus belongs to the genus Tobamovirus. In further embodiments, the rod-shaped plant virus belongs to the tobacco mosaic virus species. The tobacco mosaic virus has a capsid made from 2130 molecules of coat protein and one molecule of genomic single strand RNA 6400 bases long. The coat protein self-assembles into the rod like helical structure (16.3 proteins per helix turn) around the RNA which forms a hairpin loop structure. The protein monomer consists of 158 amino acids which are assembled into four main alpha-helices, which are joined by a prominent loop proximal to the axis of the virion. Virions are ~300 nm in length and ~18 nm in diameter. Negatively stained electron microphotographs show a distinct inner channel of ~4 nm.

In some embodiments, the plant virus is an icosahedral plant virus. Examples of icosahedral plant viruses include the virus families Geminiviridae, Luteoviridae, Bromoviridae, Phycodnaviridae, and Picornaviridae. In some embodiments, the icosahedral plan virus is from the family Picornaviridae. Plant picornaviruses are relatively small, non-enveloped, positive-stranded RNA viruses with an icosahedral capsid. Plant picornaviruses have a number of additional properties that distinguish them from other picornaviruses, and are categorized as the subfamily secoviridae. In some embodiments, the virus particles are selected from the Comovirinae virus subfamily. Examples of viruses from the Comovirinae subfamily include Cowpea mosaic virus, Broad bean wilt virus 1, and Tobacco ringspot virus. In a further embodiment, the virus particles are from the Genus *Comovirus*. A preferred example of a *Comovirus* is the cowpea mosaic virus particles.

Spherical Nanoparticles

Rod-shaped plant virus particles can be combined with other rod-shaped plant virus particles by means of a thermal transition to form an RNA-free spherical nanoparticle (SNP), also referred to herein as a spherical nanoparticle imaging platform. A spherical nanoparticle imaging platform is a spherical arrangement of the coat proteins of a plurality of rod-shaped plant virus particles linked to an imaging agent on an interior surface of the virus particle, formed by thermal transition of the rod-shaped virus particles. The SNPs can be formed from rod-shaped plant virus particles bearing imaging agents linked to the interior surface of the rod-shaped plant virus particles. SNPs can be labeled with suitable chemicals prior or post thermal transition; for example, NHS-based chemistries allow one to conjugate functional molecules to SNPs post thermal transition; the SNPs are stable and remain structurally sound after chemical modification. The SNPs including imaging agent can be formed from rod-shaped plant virus particles (e.g., TMV virus particles) by briefly heating the rod-shaped plant virus particles labeled with imaging agent on an interior surface of the virus particle. For example, the rod-shaped plant virus particles can be induced to undergo a thermal transition into SNPs by heating at about 96° C. for about 10 to about 20 seconds. Examples of suitable rod-shaped virus particles include Virgaviridae virus particles and tobacco mosaic virus particles. Any of the imaging agents described herein can be used with the spherical nanoparticles. In some embodiments, the imaging agent is a chelated lanthanide such as gadolinium.

The SNPs are formed from the coat proteins of one or more individual rod-shaped plant virus particles. In various embodiments, the SNP can be formed from about 1 to 10 virus particles, from about 10 to about 20 virus particles, from about 20 to about 30 virus particles, from about 30 to about 40 virus particles, or from about 40 to about 50 virus particles. Depending on the nature of the coat proteins, the number of virus particles incorporated, and the virus particle concentration in the solution in which the thermal transition occurs, the spherical nanoparticles can also vary in size. In some embodiments, the SNPs have a size from about 50 nm to about 800 nm. In further embodiments, the SNPs have a size from about 100 to about 300 nm, or from about 150 to about 200 nm.

Spherical nanoparticles including imaging agents such as chelated gadolinium provide several advantages. First, SNPs can include a high per-particle concentration of imaging agent. For example, SNPs can include from about 3,000 to about 30,000 imaging agents per spherical nanoparticle, with about 20,000 to about 30,000 imaging agent molecules per spherical nanoparticle in some embodiments. In addition, for MRI imaging agents such as chelated lanthanides, the SNPs including imaging agents can also exhibit very high relaxivity per particle. For example, SNPs including lanthanide imaging agents can exhibit a $T_1$ relaxivity per particle from about 10,000 mM$^{-1}$ s$^{-1}$ to about 500,000 mM$^{-1}$ s$^{-1}$ at 60 MHz, with about 350,000 mM$^{-1}$ s$^{-1}$ to about 450,000 mM$^{-1}$ s$^{-1}$ at 60 MHz in some embodiments. Finally, SNPs are more rapidly cleared from the body, which can be advantageous with imaging agents that may have increased adverse side effects when they persist within the subject after imaging.

Biocompatible Minerals

A variety of different biocompatible minerals can be used to coat the surface of the plant virus particles. Examples of biocompatible minerals include silicates, graphene, mineral trioxide, calcium phosphate, iron oxide, and carbonates. In some embodiments, the biocompatible mineral is silica (i.e., silicon dioxide). Other examples of silicates include biosilicates and calcium silicate.

A layer of biocompatible mineral coated over the exterior surface of the virus particle. The biocompatible mineral may cover all of the exterior surface of the virus particle, or it may cover a significant portion of the exterior of the virus particle. For example, the biocompatible mineral may cover at least about 50%, 60%, 70%, 80%, or at least about 90% of the surface of the exterior of the virus particle. A wide variety of different biocompatible minerals can be coated onto virus particles using eletrophoretic deposition. Boccaccini et al., J R Soc Interface, 7 Suppl 5:S581-613 (2010). Alternately, the virus particle can be coated using evaporation induced self-assembly. Tarn et al., Acc Chem. Res. 2013, 46, 792-801. The layer of biocompatible mineral should be thin to avoid adding unnecessary bulk to the virus particles. In some embodiments, the layer has a thickness from about 1 to about 100 nanometers, while in other embodiments the layer has a thickness from about 20 to about 50 nanometers.

Imaging Agents

The plant virus particle is modified to carry an imaging agent. Examples of imaging agents include fluorescent compounds, radioactive isotopes, and MRI contrast agents. For example, in some embodiments, the imaging agent is a fluorescent molecule for fluorescent imaging. The detectable group can be any material having a detectable physical or chemical property. Such imaging agents have been well-developed in the field of fluorescent imaging, magnetic resonance imaging, positive emission tomography, or immunoassays and, in general, most any imaging agent useful in such methods can be applied to the present invention. Thus, an imaging agent is any composition detectable by spectroscopic, photochemical, biochemical, immunochemical, electrical, optical or chemical means. Useful imaging agents in the present invention include magnetic beads (e.g. Dynabeads™), fluorescent dyes (e.g., fluorescein isothiocyanate, AlexaFluor555, Texas red, rhodamine, and the like), radiolabels (e.g., $^3$H, $^{14}$C, $^{35}$S, $^{125}$I, $^{121}$I, $^{112}$In, $^{99}$mTc), other imaging agents such as microbubbles (for ultrasound imaging), $^{18}$F, $^{11}$C, $^{15}$O, (for Positron emission tomography), $^{99}$mTC, $^{111}$In (for single photon emission tomography), and chelated lanthanides such as terbium, gadolinium, and europium (e.g., chelated gadolinium) or iron (for magnetic resonance imaging). The choice of imaging agent depends on the sensitivity required, the ease of conjugation with the compound, stability requirements, available instrumentation, and disposal provisions.

In some embodiments, the imaging agent is a magnetic resonance imaging agent. Disease detection using MRI is often difficult because areas of disease have similar signal intensity compared to surrounding healthy tissue. In the case of magnetic resonance imaging, the imaging agent can also be referred to as a contrast agent. Lanthanide elements are known to be useful as contrast agents. The lanthanide chemical elements comprises the fifteen metallic chemical elements with atomic numbers 57 through 71, and include lanthanum, cerium, praseodymium, neodymium, promethium, samarium, europium, gadolinium, terbium, dysprosium, holmium, erbium, thulium, ytterbium, and lutetium. Preferred lanthanides include europium, gadolinium, and terbium. In order to more readily handle these rare earth metals, the lanthanides are preferably chelated. In some embodiments, the lanthanide selected for use as a contrast agent is gadolinium, or more specifically gadolinium (III).

Contrast agents are used to enhance the differentiation between tissue regions in order to better image the tissue. The ionic relaxivity rate of a contrast agent describes its capacity for contrast enhancement. The relaxivity rate can be affected by a number of factors, including the use of a chelating agent. Unless indicated otherwise, all relaxivity measurements described herein are at 60 MHz, which is the field strength at which the relaxivity was typically measured. A clinical 3.0 Tesla magnet measures at that field strength. However, it should be noted that preclinical imaging is often done at higher magnetic field strength, and that the relaxivity can change with the field strength. The relaxivity rate per plant virus particle can also be increased by increasing the number of agent molecules that are linked to the virus particle. Plant virus particles of the invention that have been chemically modified to include contrast agents can exhibit relaxivity rates from about 10,000 to about 40,000 mM$^{-1}$ S$^{-1}$. In some embodiments, the virus particles bearing contrast agents exhibit $T_1$ relaxivity rates of at least about 10,000 mM$^{-1}$ S$^{-1}$, about 20,000 mM$^{-1}$ S$^{-1}$, about 25,000 mM$^{-1}$ S$^{-1}$, about 30,000 mM$^{-1}$ S$^{-1}$, about 35,000 mM$^{-1}$ S$^{-1}$, and about 40,000 mM$^{-1}$ S$^{-1}$ at 60 MHz.

Non-radioactive labels are often attached by indirect means. Generally, a ligand molecule (e.g., biotin) is covalently bound to the virus particle. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands.

Conjugation of Imaging Agents

The invention makes use of a plant virus particle that has been modified to carry an imaging agent. Including an imaging agent allows the virus particle to serve as a platform for the imaging agent. A plant virus particle (e.g., rod-shaped plant virus particle) that has been modified to include an imaging agent is also referred to herein as an imaging nanoparticle.

In general, imaging agents can be conjugated to the plant virus by any suitable technique, with appropriate consideration of the need for pharmacokinetic stability and reduced overall toxicity to the patient. The term "conjugating" when made in reference to an agent and a plant virus particle as used herein means covalently linking the agent to the virus subject to the single limitation that the nature and size of the agent and the site at which it is covalently linked to the virus particle do not interfere with the biodistribution of the modified virus. The imaging agent can be linked to the interior or the exterior of the virus, while in some embodiments the imaging agent is linked to both the interior and the exterior of the virus. The location of the imaging agent on the interior or exterior is governed by the amino acids of the viral coat protein that are selected as target linking sites. The interior surface of the virus particle is the inward-facing side of the virus particle, which typically faces the nucleic acid within the virus particle. The exterior surface of the virus particle is the side of the virus particle facing the environment outside of the virus particle.

The imaging agent(s) can be coupled to a plant virus particle either directly or indirectly (e.g. via a linker group). In some embodiments, the agent is directly attached to a functional group capable of reacting with the agent. For example, viral coat proteins include lysines that have a free amino group that can be capable of reacting with a carbonyl-containing group, such as an anhydride or an acid halide, or with an alkyl group containing a good leaving group (e.g., a halide). Viral coat proteins also contain glutamic and aspartic acids. The carboxylate groups of these amino acids also present attractive targets for functionalization using carbodiimide activated linker molecules; cysteines can also be present which facilitate chemical coupling via thiol-selective chemistry (e.g., maleimide-activated compounds). Further, viral coat proteins contain tyrosines, which can be modified using diazonium coupling reactions. In addition, genetic modification can be applied to introduce any desired functional residue, including non-natural amino acids, e.g. alkyne- or azide-functional groups. See Hermanson, G. T. Bioconjugation Techniques. (Academic Press, 2008) and Pokorski, J. K. and N. F. Steinmetz, Mol Pharm 8(1): 29-43 (2011), the disclosures of which are incorporated herein by reference.

Alternatively, a suitable chemical linker group can be used. A linker group can serve to increase the chemical reactivity of a substituent on either the agent or the virus particle, and thus increase the coupling efficiency. Suitable linkage chemistries include maleimidyl linkers, which can be used to link to thiol groups, isothiocyanate and succinimidyl (e.g., N-hydroxysuccinimidyl (NHS)) linkers, which can link to free amine groups, diazonium which can be used to link to phenol, and amines, which can be used to link with free acids such as carboxylate groups using carbodiimide activation. Useful functional groups are present on viral coat proteins based on the particular amino acids present, and additional groups can be designed into recombinant viral coat proteins. It will be evident to those skilled in the art that a variety of bifunctional or polyfunctional reagents, both homo- and hetero-functional (such as those described in the catalog of the Pierce Chemical Co., Rockford, Ill.), can be employed as a linker group. Coupling can be effected, for example, through amino groups, carboxyl groups, sulfhydryl groups or oxidized carbohydrate residues.

Other types of linking chemistries are also available. For example, methods for conjugating polysaccharides to peptides are exemplified by, but not limited to coupling via alpha- or epsilon-amino groups to NaIO$_4$-activated oligosaccharide (Bocher et al., J. Immunol. Methods 27, 191-202 (1997)), using squaric acid diester (1,2-diethoxycyclobutene-3,4-dione) as a coupling reagent (Tietze et al. Bioconjug Chem. 2:148-153 (1991)), coupling via a peptide linker wherein the polysaccharide has a reducing terminal and is free of carboxyl groups (U.S. Pat. No. 5,342,770), and coupling with a synthetic peptide carrier derived from human heat shock protein hsp65 (U.S. Pat. No. 5,736,146). Further methods for conjugating polysaccharides, proteins, and lipids to plant virus peptides are described by U.S. Pat. No. 7,666,624.

When attaching lanthanide imaging agents such as gadolinium ions a chelating compound is also used. Conjugation of a chelated lanthanide ion to a virus particle can decrease its molecular tumbling rate, resulting in an increased ionic relaxivity rate. A number of chelating compounds have been developed to increase the coordinated water molecules for lanthanide ions, which can almost double the relaxivity rate. Examples of effective gadolinium chelating molecules include 1,4,7,10-tetraazacyclododecane-1,4,7,10-tetraacetic acid (DOTA), diethylenetriaminopentacetate (DTPA), 1,4,7,10-tetraazacyclododecane-1,4,7-triasacetic acid (DO3A), 6-amino-6-methylperhydro-1,4-diazepinetetraacetic acid (AAZTA), and 4-carboxyamido-3,2-hydroxypyridinone (HOPA). See Gugliotta et al., Org. Biomol. Chem., 8, 4569 (2010), the disclosure of which is incorporated herein by reference. Bifunctional chelating agents including N-hydroxysuccinimide/isothiocyanates, amine, maleimide, and azide chemical linkers can be used for conjugation to amines, carboxylatic acids, thiols, and alkynes.

In some embodiments, more than one type of imaging agent can be attached to a plant virus particle. For example, a plant virus particle can be made useful as an imaging agent for two or more different visualization techniques. In further embodiments, differences in the linking sites available on the outside surface (i.e., exterior) and inside channel (i.e., interior) of the virus particle can be used to provide a virus particle with different imaging agents on the inside and outside of the virus particle. For example, the virus particle can have a first imaging agent on the inside of the particle, and a second, different imaging agent on the outside of the virus particle. The different linking sites allow different linking chemistries to be used for the interior and exterior portions of the virus particle. In further embodiments, rather than including a different imaging agent, different linking sites can be used to attach a targeting moiety to the virus particle.

The number of imaging agents that can be loaded onto the virus particle depends on the number of attachment sites available and the chemistries employed to link the agents to the virus particle. In some embodiments, each virus particle is loaded with about 500 agent molecules. In further embodiments, each virus particle is loaded with at least about 1,000, 1,500, 2,000, 2,500, 3,000, 3,500, 4,000, 4,500, or at least about 5,000 imaging agent molecules.

Targeting Moieties

In some embodiments, a targeting moiety can also be attached to the plant virus particle. By "targeting moiety" herein is meant a functional group which serves to target or direct the virus particle to a particular location, cell type, diseased tissue, or association. In general, the targeting moiety is directed against a target molecule. Thus, for example, antibodies, cell surface receptor ligands and hormones, lipids, sugars and dextrans, alcohols, bile acids, fatty acids, amino acids, peptides and nucleic acids may all be attached to localize or target the virus particle to a particular site. In some embodiments, the targeting moiety allows targeting of the plant virus particles of the invention to a particular tissue or cell type. For example, in some embodiments, the targeting moiety specifically binds to an immune cell. Preferably, the targeting moiety is linked to the exterior surface of the virus to provide easier access to the target molecule.

In some embodiments, the targeting moiety is a peptide. For example, chemotactic peptides have been used to image tissue injury and inflammation, particularly by bacterial infection; see WO 97/14443, hereby expressly incorporated by reference in its entirety. Another example, are peptides specific to fibrin or vascular cell adhesion molecules to direct the imaging probe to sites of inflammation, such as an atherosclerotic plaque. In other embodiments, the targeting moiety is an antibody. The term "antibody" includes antibody fragments, as are known in the art, including Fab $Fab_2$, single chain antibodies (Fv for example), chimeric antibodies, etc., either produced by the modification of whole antibodies or those synthesized de novo using recombinant DNA technologies. As is known to those skilled in the art, antibodies specifically bind to a particular antigen. In further embodiments, the antibody targeting moieties of the invention are humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin.

In some embodiments, the antibody is directed against a cell-surface marker on a diseased cell such as a cancer cell; that is, the target molecule is a cell surface molecule. As is known in the art, there are a wide variety of antibodies known to be differentially expressed on tumor cells, including, but not limited to, HER2. Examples of physiologically relevant carbohydrates may be used as cell-surface markers include, but are not limited to, antibodies against markers for breast cancer (CA 15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

In some embodiments, the targeting moiety is all or a portion (e.g. a binding portion) of a ligand for a cell surface receptor. Suitable ligands include, but are not limited to, all or a functional portion of the ligands that bind to a cell surface receptor selected from the group consisting of insulin receptor (insulin), insulin-like growth factor receptor (including both IGF-1 and IGF-2), growth hormone receptor, glucose transporters (particularly GLUT 4 receptor), transferrin receptor (transferrin), epidermal growth factor receptor (EGF), low density lipoprotein receptor, high density lipoprotein receptor, leptin receptor, estrogen receptor (estrogen); interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor (VEGF), PDGF receptor (PDGF), transforming growth factor receptor (including TGF-α and TGF-β), EPO receptor (EPO), TPO receptor (TPO), ciliary neurotrophic factor receptor, prolactin receptor, and T-cell receptors. Receptor ligands include ligands that bind to receptors such as cell surface receptors, which include hormones, lipids, proteins, glycoproteins, signal transducers, growth factors, cytokines, and others.

In some embodiments, the targeting moiety binds specifically to an immune cell. Examples of immune cells include neutrophiol, monocytes, macrophages, dendritic cells, natural killer cells, T-cells, and B-cells. A preferred immune cell is the macrophage. A wide variety of cell surface markers that can be used as the target for targeting moieties are known to those skilled in the art.

Imaging a Tissue Region

An additional aspect of the present invention provides a method of generating an image of a tissue region of a subject. The method includes administering to the subject a diagnostically effective amount of an imaging nanoparticle, comprising a plant virus particle having an interior surface and an exterior surface, an imaging agent that is linked to the interior and/or exterior surface, and a layer of biocompatible mineral coated over the exterior surface, and generating an image of the tissue region of the subject to which the imaging nanoparticle has been distributed. The imaging nanoparticle can include any of the specific features described herein.

In some embodiments, the imaging nanoparticle is used to target tissue in a subject without the use of a targeting moiety based on the ability of plant virus particles to preferentially accumulate in certain tissues. In particular, the plant virus particles have been shown to preferentially accumulate in diseased tissue, such as cancer tissue or inflamed tissue (e.g., atherosclerotic blood vessels). While not intending to be bound by theory, it appears that plant virus particles (e.g., rod-shaped plant virus particles) are taken up by blood components such as macrophage cells of the immune system, which subsequently accumulate in diseased tissue (e.g., a tumor or atherosclerotic blood vessel), thereby delivering the plant virus to cells at the disease site.

A tumor is an abnormal mass of tissue as a result of abnormal growth or division of cells caused by cancer. Tumors can occur in a variety of different types of tissue such as the breast, lung, brain, liver kidney, colon, and prostate, can be malignant or benign, and generally vary in size from about 1 cm to about 5 cm.

Magnetic resonance angiography (MRA) is a type of MRI that generates pictures of blood vessels (e.g., arteries) to evaluate them for stenosis (abnormal narrowing) or aneurysms (vessel wall dilatations, at risk of rupture). MRA can be used to evaluate the arteries of the neck and brain, the thoracic and abdominal aorta, the renal arteries, and the legs. Imaging nanoparticles can be used to facilitate conducting MRA of blood vessels for various uses, including evaluation of the possible development of atherosclerosis. Atherosclerosis is a chronic inflammatory response in the walls of arteries, caused largely by the accumulation of macrophages and white blood cells and promoted by low-density lipoproteins (LDL, plasma proteins that carry cholesterol and triglycerides) without adequate removal of fats and cholesterol from the macrophages by functional high-density lipoproteins (HDL). It is commonly referred to as a hardening or furring of the arteries, and is caused by the formation of multiple plaques within the arteries, which can be detected by MRA.

In order to generate an image of the tissue region, it is necessary for an effective amount of imaging agent to reach the tissue region of interest, but it is not necessary that the imaging agent be localized in this region alone. However, in some embodiments, the imaging nanoparticles are targeted or administered locally such that they are present primarily in the tissue region of interest. In some embodiments, SNPs formed from rod-shaped plant virus particles are used. Examples of images include two-dimensional cross-sectional views and three dimensional images. In some embodiments, a computer is used to analyze the data generated by the imaging agents in order to generate a visual image. The plant virus particles can include any of the virus particles described herein, such as Virgaviridae virus particles and tobacco mosaic virus particles. The tissue region can be an organ of a subject such as the heart, lungs, or blood vessels. In other embodiments, the tissue region can be diseased tissue, or tissue that is suspected of being diseased, such as a tumor or atherosclerotic tissue. Examples of imaging methods include fluoroscopy, computed tomography, positive emission tomography, and magnetic resonance imaging.

Means of detecting labels in order to generate an image are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Finally simple colorimetric labels may be detected simply by observing the color associated with the label.

"Computed tomography (CT)" refers to a diagnostic imaging tool that computes multiple x-ray cross sections to produce a cross-sectional view of the vascular system, organs, bones, and tissues. "Positive emissions tomography (PET)" refers to a diagnostic imaging tool in which the patient receives a radioactive isotopes by injection or ingestion which then computes multiple x-ray cross sections to produce a cross-sectional view of the vascular system, organs, bones, and tissues to image the radioactive tracer. These radioactive isotopes are bound to compounds or drugs that are injected into the body and enable study of the physiology of normal and abnormal tissues. "Magnetic resonance imaging (MRI)" refers to a diagnostic imaging tool using magnetic fields and radiowaves to produce a cross-sectional view of the body including the vascular system, organs, bones, and tissues. Suitable imaging agents should be used that will help generate an image of a tissue region in the context of the imaging technique being used. For example, when using magnetic resonance imaging, a suitable imaging agent is a chelated lanthanide.

In some embodiments, the imaging nanoparticles of the present invention are used for MRI. MRI provides a good contrast between the different soft tissues of the body, which makes it especially useful in imaging the brain, muscles, the heart, and cancers compared with other medical imaging techniques such as computed tomography or X-rays. An MRI scanner is a device in which the subject lies within a large, powerful magnet where the magnetic field is used to align the magnetization of some atomic nuclei in the body, and radio frequency magnetic fields are applied to systematically alter the alignment of this magnetization. This causes the nuclei to produce a rotating magnetic field detectable by the scanner and this information is recorded to construct an image of a tissue region. Magnetic field gradients cause nuclei at different locations to process at different speeds, allowing spatial information to be recovered using Fourier analysis of the measured signal. By using gradients in different directions, 2D images or 3D volumes can be obtained in any arbitrary orientation Various different types of MRI scans can be conducted, including $T_1$-weighted MRI, $T_2$-weighted MRI, and spin density weighted MRI. In some embodiments, the viral imaging agents of the invention are used as contrast agents to facilitate a $T_1$-weighted MRI scan. $T_1$-weighted scans refer to a set of standard scans that depict differences in the spin-lattice (or $T_1$) relaxation time of various tissues within the body. $T_1$ weighted images can be acquired using either spin echo or gradient-echo sequences. $T_1$-weighted contrast can be increased with the application of an inversion recovery RF pulse. Gradient-echo based $T_1$-weighted sequences can be acquired very rapidly because of their ability to use short inter-pulse repetition times (TR).

Immunogenicity of Imaging Nanoparticles

Administering viral particles to a subject is known to sometimes generate an immune response. An "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, invading pathogens, cells or tissues infected with pathogens, or, in cases of autoimmunity or pathological inflammation, normal human cells or tissues. Components of an immune response can be detected in vitro by various methods that are well known to those of ordinary skill in the art.

Figure 1B:
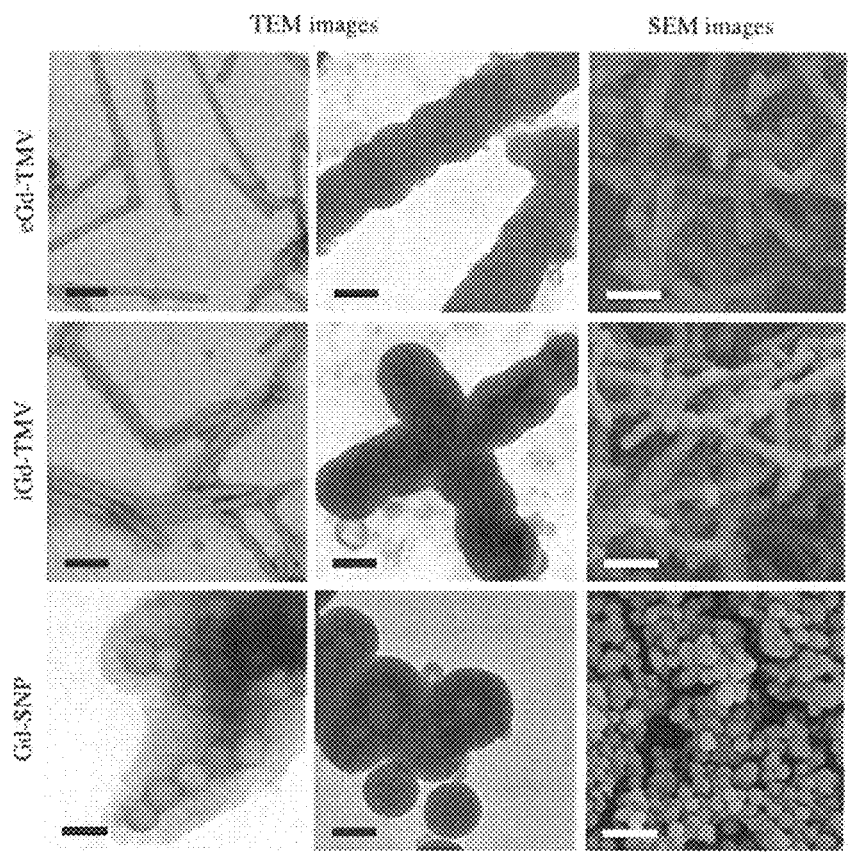
Figure 6:
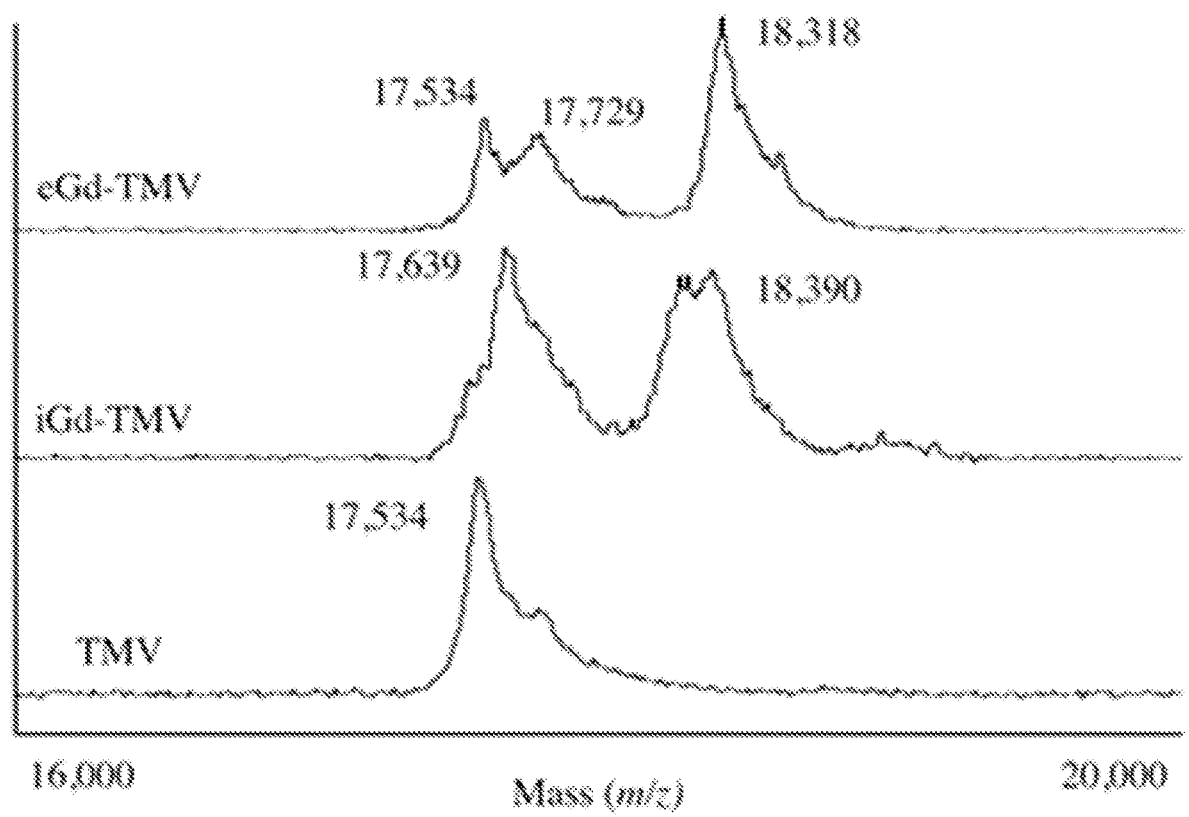
FIG. 6 provides a graph showing the MALDI-TOF MS spectra for modified TMV particles. Peak assignments: native TMV=17,534 m/z; iGd-TMV=17,639 m/z (alkyne-modified) and 18,390 m/z (Gd(DOTA) modified); eGd-TMV=17,534 m/z (unmodified), 17,729 m/z (alkyne modified), and 18,318 m/z (Gd(DOTA) modified).

An advantage of the imaging nanoparticles of the present invention is that they exhibit decreased immunogenicity as a result of including a layer of biocompatible mineral. As noted above, viral particles are known to often induce an immune response when administered to a subject. Coating the plant virus particles with a biocompatible mineral decreases or in some cases eliminates this immune response. In some embodiments, the biocompatible mineral can decrease the immune response by at least 10%, 20%, 30%, 40%, 50%, 60%, 70%, 80%, 90%, or in some cases by 100%. While not intending to be bound by theory, the decreased immunogenicity exhibited by viral particles coated with a biocompatible mineral may occur as a result of a decreased ability for the viral particles to be recognized by antibodies.

Administration and Formulation of Imaging Nanoparticles

In some embodiments, the imaging nanoparticles are administered together with a pharmaceutically acceptable carrier to provide a pharmaceutical formulation. Pharmaceutically acceptable carriers enable the imaging nanoparticles to be delivered to the subject in an effective manner while minimizing side effects, and can include a variety of diluents or excipients known to those of ordinary skill in the art. Formulations include, but are not limited to, those suitable for oral, rectal, vaginal, topical, nasal, ophthalmic, or parental (including subcutaneous, intramuscular, intraperitoneal, intratumoral, and intravenous) administration. For example, for parenteral administration, isotonic saline is preferred. For topical administration, a cream, including a carrier such as dimethylsulfoxide (DMSO), or other agents typically found in topical creams that do not block or inhibit activity of the compound, can be used. Other suitable carriers include, but are not limited to, distilled water, physiological phosphate-buffered saline, Ringer's solutions, alcohol, dextrose solution, and Hank's solution. In addition, the pharmaceutical composition or formulation may also include other carriers, adjuvants, or nontoxic, nontherapeutic, nonimmunogenic stabilizers and the like.

The formulations may be conveniently presented in unit dosage form and may be prepared by any of the methods well known in the art of pharmacy. Preferably, such methods include the step of bringing the imaging nanoparticle into association with a pharmaceutically acceptable carrier that constitutes one or more accessory ingredients. In general, the formulations are prepared by uniformly and intimately bringing the imaging nanoparticle into association with a liquid carrier, a finely divided solid carrier, or both, and then, if necessary, shaping the product into the desired formulations.

Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949. An amount adequate to accomplish imaging is a diagnostically effective amount. Effective doses of the imaging nanoparticle vary depending upon many different factors, including means of administration, target site, physiological state of the patient, whether the patient is human or an animal, other medications administered.

For administration for imaging in a mammalian subject utilizing an imaging nanoparticle, the dosage of the imaging agent ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. A suitable amount of virus particle is used to provide the desired dosage. An exemplary treatment regime entails administration once per every two weeks or once a month or once every 3 to 6 months. The imaging nanoparticle can be administered on multiple occasions. Alternatively, the imaging nanoparticle can be administered as a sustained release formulation, in which case less frequent administration is required.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

The present invention is illustrated by the following example. It is to be understood that the particular example, materials, amounts, and procedures are to be interpreted broadly in accordance with the scope and spirit of the invention as set forth herein.

EXAMPLE

Example 1: Silica-Coated Gd(DOTA)-Loaded Protein Nanoparticles Enable Magnetic Resonance Imaging of Macrophages The molecular imaging of in vivo targets allows non-invasive disease diagnosis. Nanoparticles offer a promising platform for molecular imaging because they can deliver large payloads of imaging reagents to the site of disease. Magnetic resonance imaging (MRI) is often preferred for clinical diagnosis because it uses non-ionizing radiation and offers both high spatial resolution and excellent penetration. The inventors have explored the use of plant viruses as the basis of for MRI contrast reagents, specifically Tobacco mosaic virus (TMV), which can assemble to form either stiff rods or spheres. TMV particles were loaded with paramagnetic Gd ions, increasing the ionic relaxivity compared to free Gd ions. The loaded TMV particles were then coated with silica maintaining high relaxivities. Interestingly, it was found that when Gd(DOTA) was loaded into the interior channel of TMV and the exterior was coated with silica, the T1 relaxivities increased by three-fold from 10.9 $mM^{-1}$ $s^{-1}$ to 29.7 $mM^{-1}$ $s^{-1}$ at 60 MHz compared to uncoated Gd-loaded TMV. To test the performance of the contrast agents in a biological setting, the inventors focused on interactions with macrophages because the active or passive targeting of immune cells is a popular strategy to investigate the cellular components involved in disease progression associated with inflammation. In vitro assays and phantom MRI experiments indicate efficient targeting and imaging of macrophages, enhanced contrast-to-noise ratio was observed by shape-engineering (SNP>TMV) and silica-coating (Si-TMV/SNP>TMV/SNP). Because plant viruses are in the food chain, antibodies may be prevalent in the population. It was therefore investigated whether the silica-coating could prevent antibody recognition; indeed the data indicate that mineralization can be used as a stealth coating option to reduce clearance. The inventors therefore conclude that the silica-coated protein-based contrast agent may provide an interesting candidate material for further investigation for in vivo delineation of disease through macrophage imaging.

Results and Discussion

The nanoparticles were based on a mutant of TMV (S152K, TMVlys) that displays a reactive amine-functional lysine group at the solvent-exposed C-terminus of the coat protein. Geiger et al., Nanoscale. 2013; 5(9):3808-3816. TMVlys was produced in *Nicotiana benthamiana* plants with a yield of 5 mg pure TMVlys particles per gram of infected leaf material. TMVlys comprises 2130 identical coat proteins arranged helically into a 300-nm soft-matter rod, 18 nm in diameter with a 4-nm internal channel. TMVlys was modified with paramagnetic $Gd^{III}$ chelated to azido-mono amide-1,4,7,10-tetraazacyclododecane-N,N',N",N"'-tetraacetic acid (DOTA-azide) to yield the MRI contrast-enhancement agent. Bruckman et al., Journal of Materials Chemistry B. 2013; 1(10):1482. The bioconjugation of Gd(DOTA) to the internal and external surfaces of TMVlys is described in detail in the Supporting Information and FIG. 5. Briefly, terminal alkyne functionality was provided by modifying the tyrosine (TYR139) or glutamic acid (GLU 97/106) residues. Bruckman et al., ACS Biomater Sci Eng., 2015; 1(1):13-8. Gd(DOTA) was attached to the terminal alkynes using a copper-catalyzed azide-alkyne cycloaddition reaction, forming internal Gd(DOTA) TMVlys (iGd-TMV) or external Gd(DOTA) TMVlys (eGd-TMV). TMVlys-based spherical nanoparticles (SNPs) were produced by heating iGd-TMV to 96° C. for 60 s using a PCR thermocycler, forming Gd-SNP. Gd(DOTA) labeling efficiency (FIG. 2A) was characterized by inductively-coupled plasma optical emission spectroscopy (ICP-OES) and matrix assisted laser desorption-ionization time-of-flight mass spectrometry (MALDI-TOF MS) as shown in FIG. 6. TEM imaging was used to confirm the structural integrity of the TMV rods and spheres after chemical modification (FIG. 1B). The TMV rods were modified with an average of 1000 Gd(DOTA) molecules per particle in both the internal and external labeling configurations. Similar loading density was achieved for SNPs, with 976 Gd(DOTA) per 2130 coat proteins (based on absorbance) on a particle with a diameter of ~75 nm and a density of 1.43 g/cm$^3$, compared to 1.31 g/cm$^3$ for the TMV rods. Dobrov et al., Journal of Biomolecular Structure and Dynamics. 2014; 32(5):701-8. This corresponds to an estimated 7074 coat proteins per sphere, yielding just over 3000 Gd(DOTA) labels per SNP.

Figure 7:
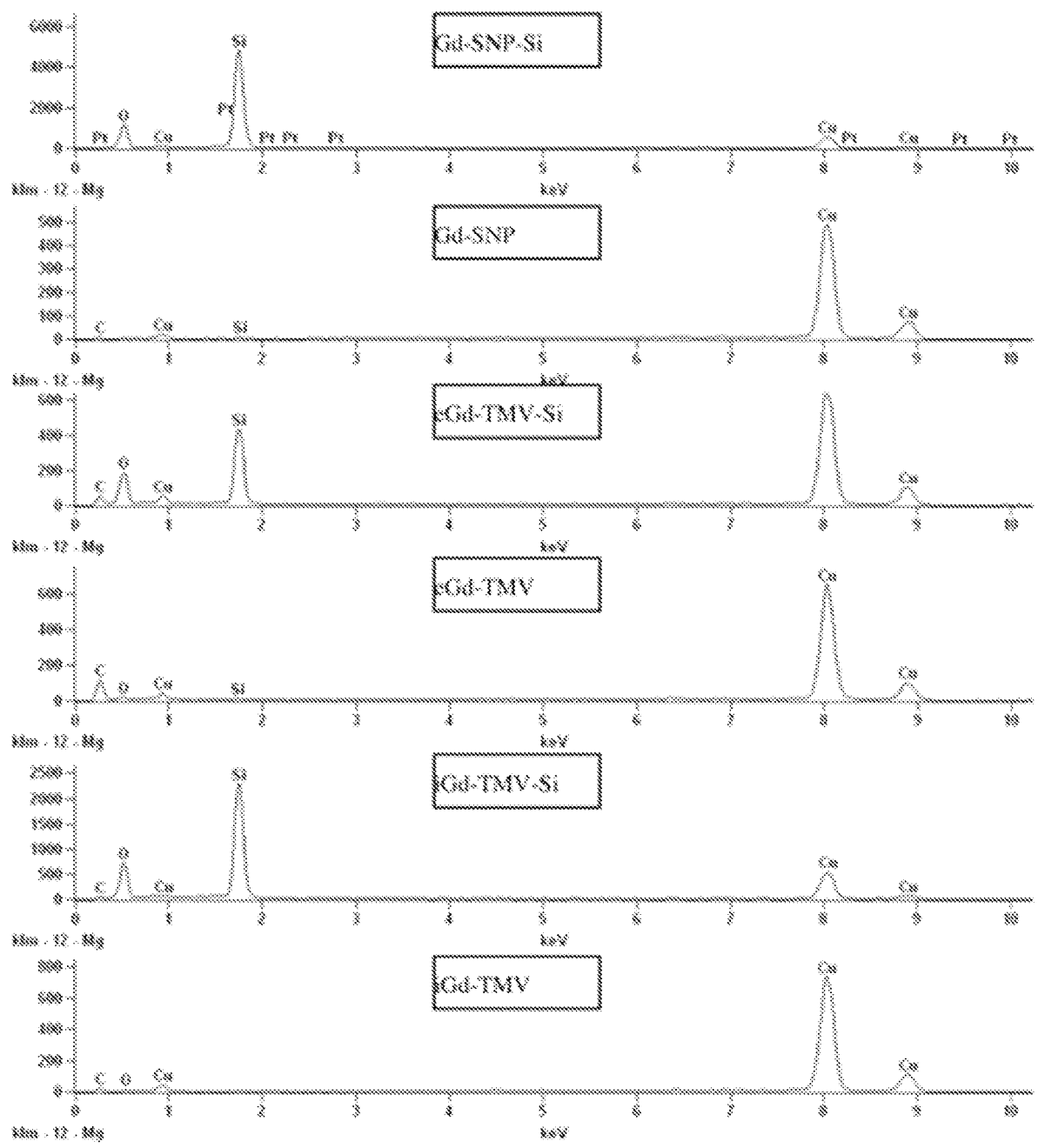
FIG. 7 provides a graph showing the electron dispersion spectra of TMV before and after mineralization confirming the presence of silica after mineralization.

Silica coatings were introduced as described, with modifications. Stober et al., Journal of Colloid and Interface Science. 1968; 26(1):62-69. Briefly, 1 ml tetraethyl orthosilicate (TEOS) as a 10% v/v stock in ethanol was mixed with 4 ml 5 M NH$_4$OH and 1 ml of modified TMVlys or SNPs (1 mg/ml in water) and diluted to 20 ml with ice-cold ethanol. The reaction was allowed to proceed overnight. The resulting Si coat was ~65 nm deep, increasing the thickness of the nanoparticles to ~150 nm as shown by TEM and SEM (FIG. 1B). The TMVlys mutant allowed the formation of a higher-quality silica coating compared to native TMV, because the positive charge of the solvent-exposed amine groups favored the nucleation of silica catalyzed by TEOS. The presence of silica was confirmed by TEM using electron dispersion spectroscopy (EDS) as shown in FIG. 7. Silica mineralization presented the following challenges: First, the proportion of ethanol must be ~90% after all reactants have been added because lower concentrations increase the abundance of free silica particles, and high concentrations result in much thinner coatings. Additionally, salt must be removed from the TMV solution before mineralization. Sonication reduced aggregation and improved the dispersion of the mineralized particles. This is consistent with previous reports describing the silica mineralization of TMV (Fowler et al., Advanced Materials, 2001; 13(16):1266-9), fd phage (Zhang Z, Buitenhuis J., Small. 2007; 3(3):424-8), and other nanoparticles (Liu et al., Advanced Materials. 2014; 27(3): 479-97). Silica is ideal as a coating material due to its biocompatibility, ease of surface functionalization, versatility, and stability. Tamba et al., European Journal of Pharmaceutical Sciences. 2015; 71:46-55.

Next, the longitudinal proton relaxivity of Gd(DOTA)-modified TMV rods and spheres (SNPs) was measured using a standard inversion recovery sequence on a 60 MHz relaxometer (Bruker) at 37° C. (FIG. 2). Previously, the inventors found that TMV externally modified with Gd(DOTA) had a higher ionic relaxivity than internally-modified particles due to increased stiffness of the tyrosine residue and better bulk water accessibility. Bruckman et al., Journal of Materials Chemistry B. 2013; 1(10):1482. Overall, the same trend was observed in the present study.

Figure 8:
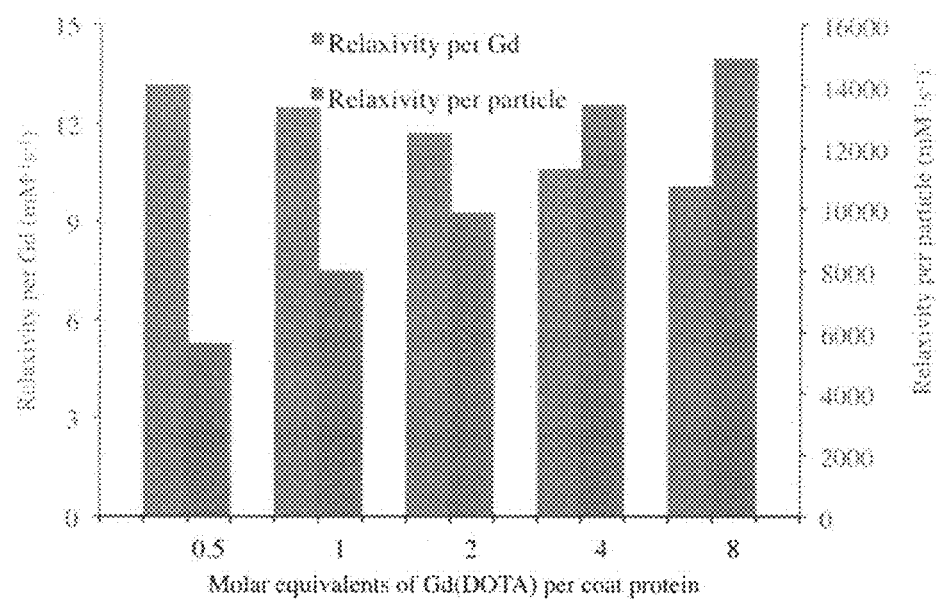
FIG. 8 provides a table and graph showing the relaxivity of TMV rods loaded with varying amounts of Gd(DOTA), where eq=molar equivalents. Measurements at 60 MHz. Relaxivity values in $mM^{-1}$ $s^{-1}$.

Throughout the investigation, some batch-to-batch variations in the ionic relaxivity were noted when TMV samples were compared with different Gd(DOTA) loading rates. Therefore, the inventors set out to determine whether the Gd(DOTA) density affected the ionic relaxivity of the particles. TMV rods with Gd(DOTA) loads ranging from 429 to 1477 Gd per particle were prepared and the ionic relaxivities were determined (FIG. 8). An inverse correlation between ionic relaxivity and Gd(DOTA) density was found. Although the per-particle relaxivity increased at higher Gd density, the ionic relaxivity decreased at higher Gd density. If the Gd(DOTA) ions are distributed in a statistically random manner, the lower-density formulation may offer greater inter-Gd(DOTA) spacing and therefore may increase the number of water molecules showing interactions at any given time. Others have shown that greater spacing between Gd ions (lower density) can increase overall relaxivity by increasing the transverse electronic relaxivity of the ions. Interactions between nearby paramagnetic centers increase the electronic relaxation of the electron spins of Gd ions, thereby reducing the water relaxivity. Nicolle et al., Magnetic Resonance in Chemistry. 2003; 41(10):794-9. For example, micelles fully loaded (100%) with chelated Gd were able to achieve relaxivities of 30.0 mM$^{-1}$ s$^{-1}$ at 20 MHz, whereas micelles loaded with 98% Y and 2% Gd achieved a relaxivity of 41.4 mM$^{-1}$ s$^{-1}$ at 20 MHz. Gianolio et al., Chemistry—A European Journal. 2007; 13(20):5785-97. Alternatively, if one considers iGd-TMV and assumes the labeling density increases at the open ends, this would allow for more efficient water exchange with the bulk water surrounding the TMV rod without limiting water exchange in the 4-nm internal channel. Indeed, similar trends have been reported with mesoporous silica nanoparticles labeled with Gd when the entrance to the pores is compared to the entire structure. Davis et al., Journal of Materials Chemistry. 2012; 22(43):22848-50.

Next, the relaxivities of mineralized TMV rods and SNPs versus their native counterparts were compared. The ionic and per particle relaxivities remained consistent for eGd-TMV (23.5 vs 24.8 mM$^{-1}$ s$^{-1}$) and SNP (17.7 vs 16.5 mM$^{-1}$ s$^{-1}$) following silica coating (FIG. 2). Silica mineralization alone did not change the relaxivity compared to concentration-matched unlabeled TMVlys particles (FIG. 2F). In stark contrast, a nearly three-fold increase in relaxivity was observed for mineralized versus native iGd-TMV particles, i.e. there was an increase from 10.9 to 29.7 mM$^{-1}$ s$^{-1}$ at 60 MHz which is presented as a bar chart (FIG. 2B) and in the form of relaxivity curves (FIG. 2C-F).

Figures 9A, 9B, 9C:
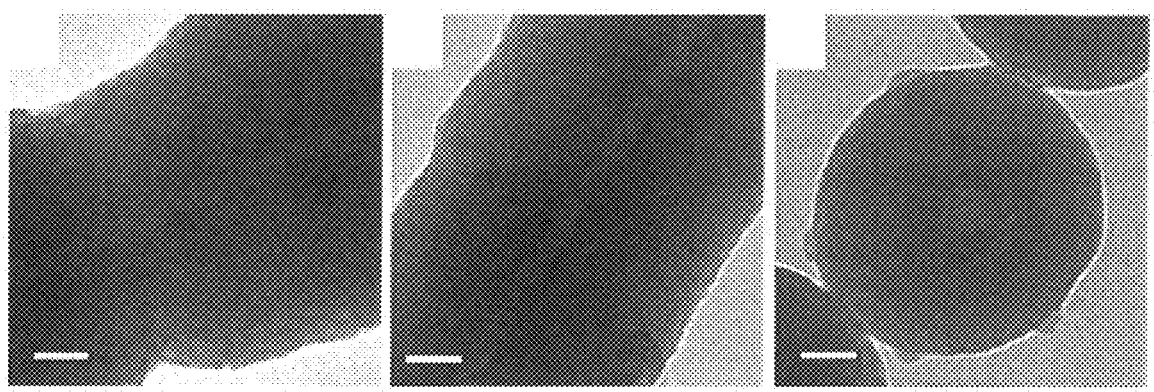
FIG. 9 (A-C) provides high-resolution TEM images of (A) iGd-TMV-Si, (B) eGd-TMV-Si, and (C) Gd-SNP-Si showing dense silica coat. Scale bar=25 nm.

Two factors may promote this increased relaxivity. First, mineralization around the TMV scaffold creates a dense surface coating that may trap bulk water inside the 4-nm channel resulting in differential water flux connecting the bulk surrounding water and the bulk internal water, maintaining and increasing the molecular interactions between Gd molecules and internal bulk water, therefore increasing the relaxivity of iGd-TMV but not eGd-TMV. Given that the silica-coated eGd-TMV and Gd-SNP formulations exhibited T$_1$ values comparable to their native forms suggests that mesoporous silica is formed enabling water exchange through the silica coat. High-resolution TEM confirms the formation of mesoporous silica shells on the TMV rods and spheres (FIG. 9). Second, particle stiffness increases when the silica coating is applied, and this may increase the relaxivity by inhibiting the molecular tumbling of Gd(DOTA). Nanoparticle rigidity can be calculated using the Lipari-Szabo approach, which identifies an order parameter for the local and global rotations with limiting values $0<S^2<1$, where 1 is a completely rigid nanoparticle and 0 is a fully independent contrast agent. Verwilst et al., Chemical Society Reviews. 2015; 44(7):1791-1806. Stiffer nanoparticles have higher order parameter values ($S^2$) and therefore yield a higher ionic relaxivity. Botta M, Tei L., European Journal of Inorganic Chemistry. 2012; 2012(12):1945-60.

Figure 3A:
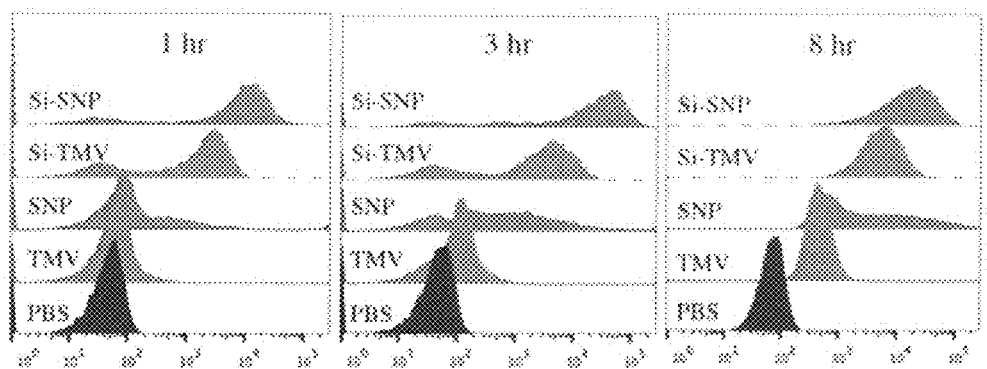
FIG. 3 (A-D) provides graphs and images showing TMV, SNP, Si-TMV and Si-SNP interactions with RAW 264.7 cells 1, 3, and 8 h after exposure using fluorescent TMV and SNP formulations, with (A) providing histograms from flow cytometry studies; (B) providing mean intensity plotted versus time and per particle formulation as a quantitative measure of cell interactions; (C) providing MRI phantom images of RAW 264.7 cell pellets 8 h after binding with TMV, SNP, Si-TMV and Si-SNP. Gd(DOTA)-labeled TMV and SNP formulations were incubated with RAW 264.7 cells for 8 h, then cells were washed and pelleted prior to obtaining MRI images using a 7.0 T (300 MHz) MRI (Bruker BioSpec 70/30USR). The arrow indicates the cell pellets, a positive signal shows as bright pixels; and (D) providing a graph showing cell interactions were quantified by contrast-to-noise (CNR) ratio of the MRI phantom image (cell pellets vs. medium).
Figure 3B:
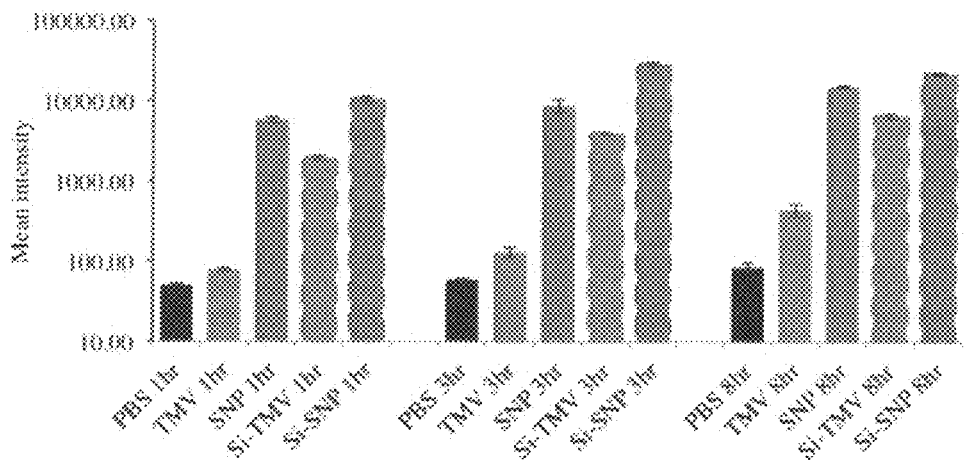
Figure 3C:
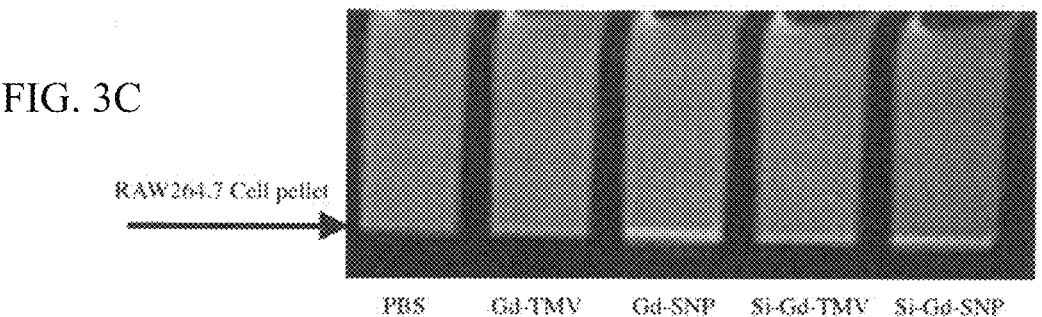
Figure 3D:
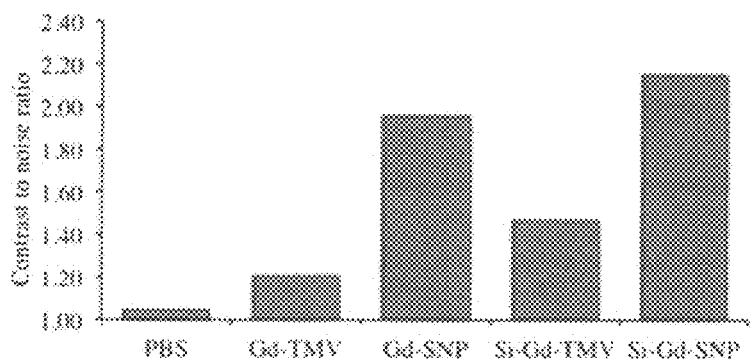

To test the performance of the contrast agents in a biological setting, the inventors focused on interactions with macrophages because the active or passive targeting of immune cells is a popular strategy to investigate the cellular components involved in disease progression. For example, targeting macrophages in cardiovascular disease can provide insight into the composition of atherosclerotic plaques and may facilitate risk stratification. A macrophage-rich and lipid-rich plaque with a thin fibrous cap may indicate a plaque vulnerable to rupture. Kooi et al., Circulation. 2003; 107(19):2453-8. RAW 264.7 murine macrophages were therefore used as a model system. Nel et al., Nature Materials. 2009; 8(7):543-57. The uptake of TMV rods and spheres was tested before and after mineralization by flow cytometry using fluorescence-labeled particles (FIGS. 3A and 3B) and then tested the Gd(DOTA)-labeled formulations in MRI experiments (FIGS. 3C and 3D). The labeling strategy and characterization of fluorescent particles is described in the Methods section.

Time-course flow cytometry showed that the silica coating significantly increased the number of interactions between macrophages and the TMV nanoparticles, regardless of their shape (FIG. 3A) agreeing with previous reports showing that macrophages rapidly scavenge silica nanoparticles. Zhu et al., Nanoscale. 2014; 6(19):11462-72. The non-coated SNPs were much more readily taken up by the macrophages than TMVlys rods (FIG. 3A). This is consistent with a recent study by the inventors showing that macrophages interact more efficiently with TMV particles with a low aspect ratio. Shukla et al., Adv Healthc Mater. 2015; 4(6):874-882. The high aspect ratio of the elongated stiff rod promotes immune evasion by inhibiting phagocytosis. This is a well-known phenomenon in nanomedicine and can be advantageous if cellular or molecular components other than macrophages are the desired target. Wen et al., Journal of Biological Physics. 2013; 39(2):301-25.

The inventors next investigated whether the Gd-labeled TMV and SNP formulations could be used to detect macrophages in a pre-clinical MRI scanner (FIG. 3C). Briefly, cells were incubated with the different MRI contrast agents and controls, and were then pelleted by centrifugation and analyzed using a 7.0 T (300 MHz) MRI (Bruker BioSpec 70/30USR). Following multiple scouting scans, a $T_1$-weighted Multi Slice Multi Echo (MSME) sequence was used with the following parameters: TR/TE=600/8.0 ms, 1 mm thickness, four averages, matrix=128×128, field of view=2.98 cm. Exported DICOM images were analyzed with the free open software OsiriX.

Figure 10A:
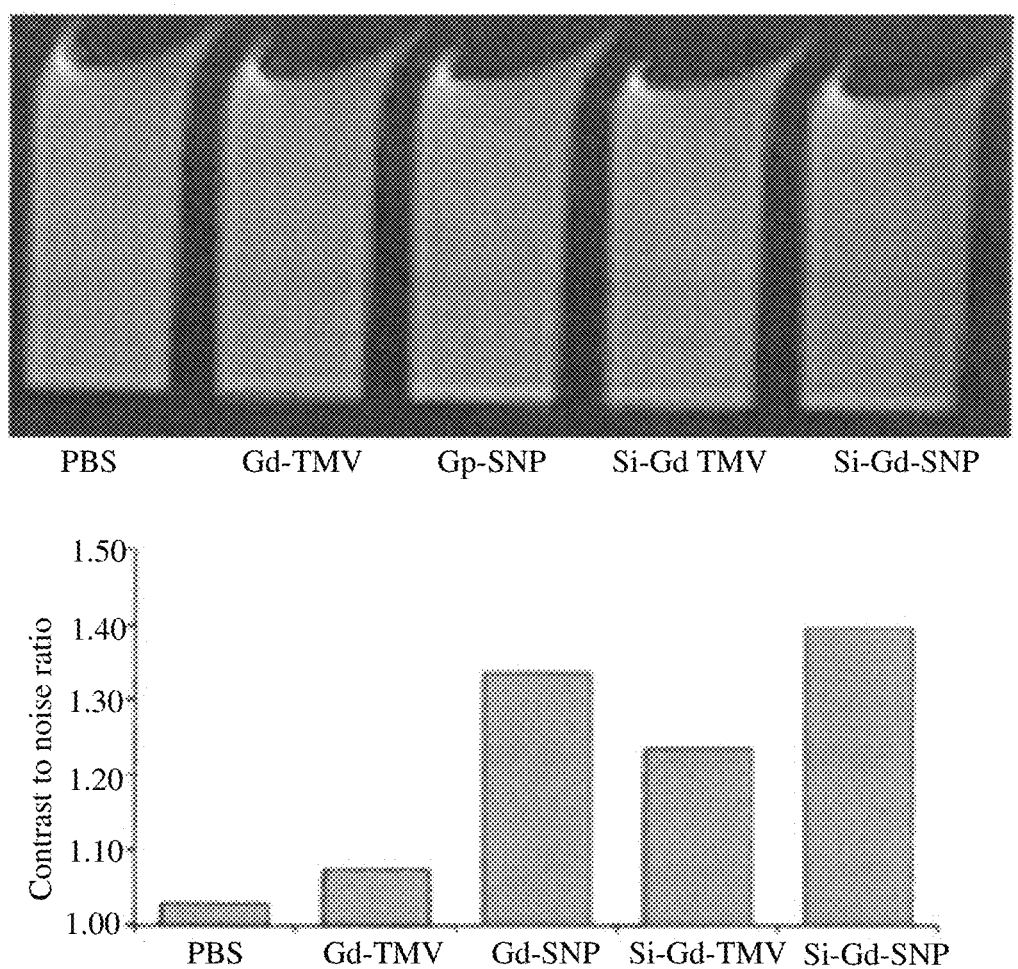
FIG. 10 (A-C) provides graphs and images; top panels: MRI phantom images of RAW 264.7 cell pellets 8 h after binding with Gd-TMV, Gd-SNP, Si-Gd-TMV and Si-Gd-SNP. Gd(DOTA)-labeled TMV and SNP formulations were incubated with RAW 264.7 cells for 8 h, then cells were washed and pelleted prior to obtaining MRI images using a 7.0 T (300 MHz) MRI (Bruker BioSpec 70/30USR). In A and B, 1,000,000 cells were incubated with (A) 250,000 VNP per cell and (B) 2,500,000 VNP per cell. In panel C, 5,000,000 cells were incubated with 1,000,000 VNP per cell. Bottom panels: Cell interactions were quantified by contrast-to-noise (CNR) ratio of the MRI phantom image (cell pellets vs. medium).
Figure 10B:
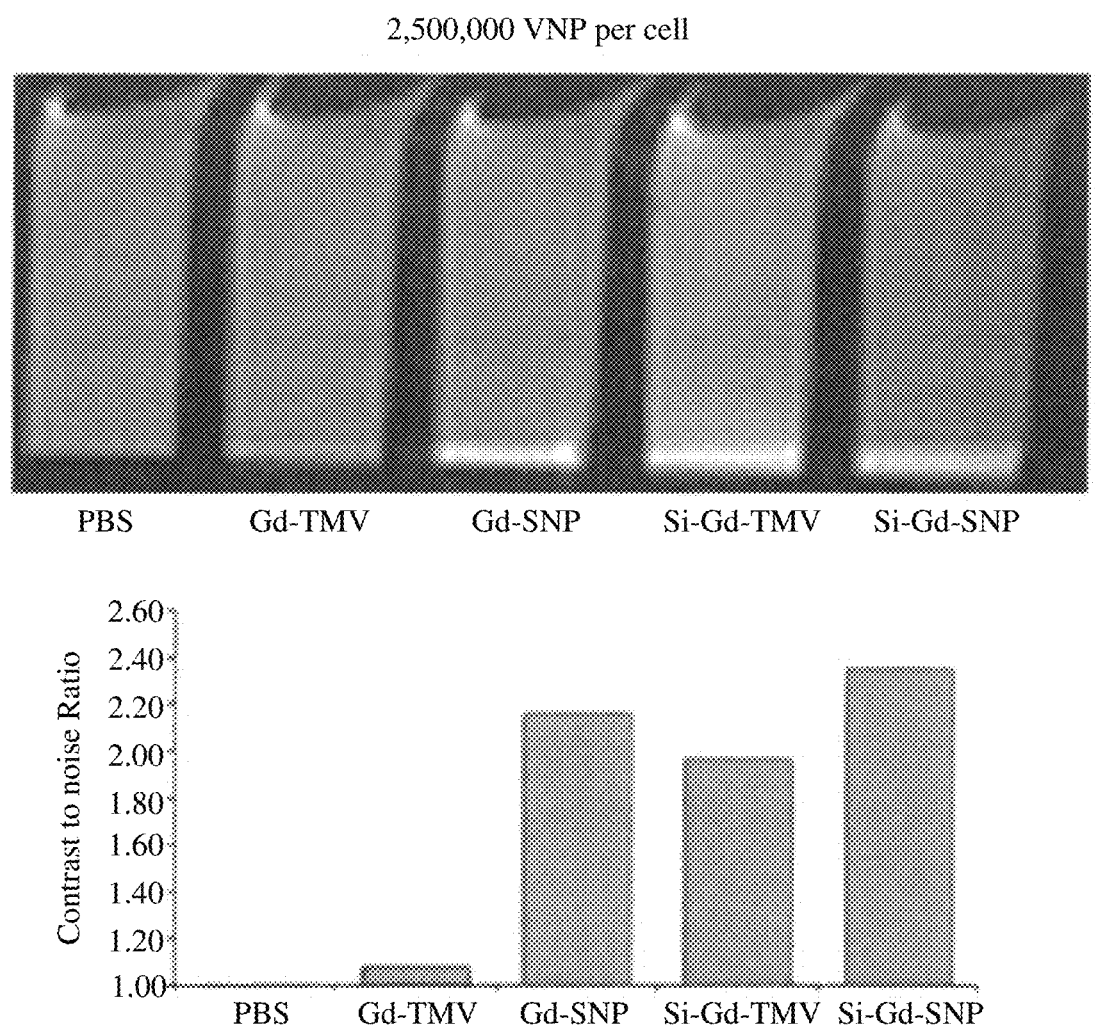
Figure 10C:
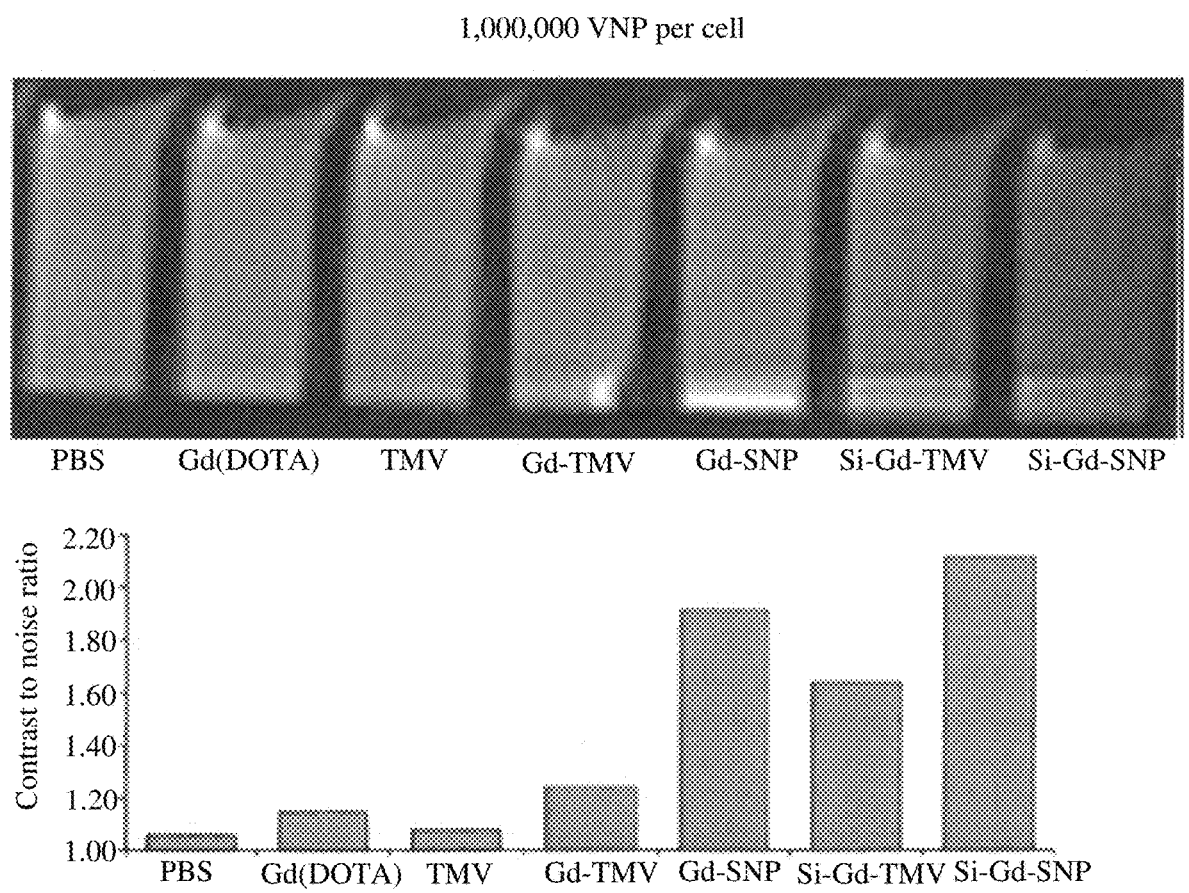

Macrophages were quantified by measuring the contrast-to-noise ratio (CNR) of cell pellets compared to the buffer solution for each well. It was found that silica-coated TMV rods and SNPs showed higher CNRs than their non-mineralized counterparts (FIG. 3D), which is consistent with the interactions observed by flow cytometry (FIG. 3B). Additionally, SNPs yielded higher CNRs than TMV rods confirming that SNPs target macrophages more efficiently than rods. The experiments were reproducible over a range of cell and particle concentrations (FIG. 10).

Together, these results demonstrate that SNP, Si-TMV and Si-SNP particles are suitable for the imaging of macrophage-rich diseases. The inventors have previously shown that targeted rod-shaped TMV particles are appropriate for MRI applied to vasculature molecular markers in atherosclerotic plaques(14). TMV rods could therefore be combined with SNPs to image molecular markers and macrophages, providing a powerful tool to facilitate risk stratification and the prognosis of atherosclerosis patients.

Lastly, the inventors set out to determine whether the silica coating would protect the TMV protein-based contrast agents from antibody recognition. VNPs, much like other protein-based nanoparticles, are prone to elicit the production of VNP-specific antibodies when introduced as 'naked' versions into the body. Furthermore, early research has shown that TMV-specific antibodies are prevalent due to presence of TMV in food and cigarettes. Therefore, they investigated whether the silica shell would protect TMV (and SNP) from recognition by the immune system. This is an important requirement in translational applications because antibody binding can interfere with target recognition and alter the fate of nanoparticle-based MRI contrast-enhancing reagents, particularly if repeat administration is necessary.

To determine the ability of the thick silica coating to prevent antibody recognition, immunogold staining experiments were carried out in which TMV, SNP, Si-TMV or Si-SNP were deposited on TEM grids followed by the application of TMV-specific antibodies and detection using 10-nm gold immunoconjugate secondary antibodies (FIG. 4, see Supporting Information for details). Accordingly, it was found that the non-coated SNP and TMV particles were efficiently recognized by the antibodies, whereas the silica-coated TMV and SNP formulations were shielded from antibody recognition. This was confirmed by testing mixed preparations of TMV and Si-TMV, which resulted in the specific recognition of the non-coated TMV particles (FIG. 4E). Silica coatings could therefore be applied as an alternative to polyethylene glycol (PEG) shielding to avoid antibody recognition. The inventors have previously shown that PEG shielding yields stealth VNPs that are not recognized by antibodies. Lee et al., Acta Biomater. 2015; 19:166-179. Whereas Si is known to improve the biocompatibility and reduce the toxicity nanoparticles based on gold, iron oxide and quantum dots, this is the first demonstration that Si can also circumvent immune surveillance.

Conclusion

Rod-shaped and spherical silica-coated TMV nanoparticles loaded with Gd(DOTA) were synthesized. Silica-coated contrast agents maintained high relaxivities, therefore providing a potential candidate material for MRI applications. Interestingly, it was found that the mineralization of TMV rods labeled internally with Gd(DOTA) increased the ionic relaxivity of the particles three-fold compared to non-mineralized particles, potentially reflecting the increased particle stiffness. Medical relevance was determined in vitro using the murine macrophage cell line RAW 264.7. These studies serve as a proof-of-concept; detection and imaging of macrophages may aid diagnosis and prognosis of disease associated with inflammation, such as cardiovascular diseases. Imaging studies demonstrate increased macrophage targeting as a function of nanoparticle shape and surface coating with SNP>TMV and Si-coated SNP/TMV>native SNP/TMV. Lastly, the inventors demonstrate that the silica-coating effectively reduced antibody binding, which is important for the translational development of these MRI contrast agents. This versatile mineralization protocol could also be applied to other platforms for biological macromolecule cargo delivery to reduce immunogenicity and may improve MRI contrast relaxivity.

Methods

TMV Manufacturing

Propagation. The TMV lysine mutant S152K was propagated in *Nicotiana benthamiana* plants and recovered, with a yield of 5 mg TMV per gram infected leaf material, using established extraction methods. M. A. Bruckman and N. F. Steinmetz, Methods in molecular biology, 2014, 1108, 173-185.

The concentration of TMV in plant extracts was determined by UV/vis spectroscopy ($\varepsilon_{260nm}$=3.0 mg$^{-1}$ mL cm$^{-1}$) and virus integrity was verified by TEM and SEM imaging.

Bioconjugation. Gd(DOTA)-labeled particles were prepared as previously described. Bruckman et al., Journal of Materials Chemistry B, 2013, 1, 1482. Briefly, the TMV external surface was modified with a diazonium salt generated from 3-ethynylaniline (25 molar equivalents (eq), pH=8.5, 30 min) to incorporate a terminal alkyne. Similarly, the internal channel was modified in the same way by mixing propargylamine (50 eq) with ethyldimethylpropyl-carbodiimide (EDC, 100 eq) and n-hydroxybenzotriazole (HOBt, 50 eq) for 24 h. Gd was chelated to azido-mono amide-1,4,7,10-tetraazacyclododecane-N,N',N'',N'''-tetraacetic acid (DOTA-azide, Macrocyclics) as previously described. Bruckman et al., Journal of Materials Chemistry B, 2013, 1, 1482. Briefly, a 1:1 mixture of GdCl$_3$ and DOTA-azide in water was mixed at room temperature for 3 days while maintaining the pH at 6-7 (tested using pH paper). After 3 days, the pH was increased to 9-10 and the precipitate was removed by centrifugation. Efficient conjugation of Gd(DOTA) azide to TMV terminal alkyne groups was accomplished by copper-catalyzed azide-alkyne cycloaddition (CuAAC) to form TMV particles with Gd-conjugated externally (eGd-TMV) or internally (iGd-TMV). Alkyne-labeled TMV (2 mg/mL) in 0.1 M potassium phosphate buffer (pH 7.0) was mixed with Gd(DOTA) azide (2 eq), aminoguanidine (2 mM), ascorbic acid (2 mM) and copper sulfate (1 mM) for 30 min on ice. The reaction mix was purified by ultracentrifugation in a 10-40% sucrose gradient, and analyzed by TEM and MALDI-TOF MS. For flow cytometry experiments, sulfo-Cy5 azide (Lumiprobe) was used in place of Gd(DOTA) azide to synthesize internally-labeled Cy5-TMV.

Thermal transition to SNP. The standard protocol for thermal transition from native TMV rods to SNPs involves heating a sample of TMV rods (0.3 mg mL$^{-1}$) for 60 s at 96° C. in a Peltier thermal cycler. SNPs are then recovered by centrifugation at 42,000 rpm for 2 h.

Mineralization. One mL of TMV or SNP particles (1 mg mL$^{-1}$) was added to 18 mL ethanol on ice and mixed in 1 mL TEOS (10% (v/v) in ethanol) and 4 mL 5 M NH$_4$OH, alternating every 15 min for 1 h. The reaction was incubated at 4° C. for 18 h followed by centrifugation at 3000 rpm for 20 min. The samples were washed with water and centrifuged again followed by overnight dialysis against water.

Particle Characterization

Inductively-coupled plasma optical emission spectroscopy (ICP-OES). The Gd loading of modified TMVs or SNPs before and after mineralization was determined by ICP-OES. Samples were diluted to give a protein concentration of 0.1 mg mL$^{-1}$ in pure water and analyzed immediately.

Relaxivity. The ionic relaxivity of the Gd(DOTA)-loaded TMVs and SNPs was tested using a Bruker Minispec mq60 relaxometer at 60 MHz. A standard inversion recovery sequence was used to determine the $T_1$.

Transmission electron microscopy (TEM). Drops of TMV rods or SNPs before and after mineralization (0.2 mg mL$^{-1}$ in 5 mL deionized water) were placed on copper TEM grids, adsorbed for 5 min, washed with deionized water, and negatively stained with 2% (w/v) uranyl acetate for 2 min. Samples were examined by energy dispersive X-ray spectroscopy using a Zeiss Libra 200FE transmission electron microscope operated at 200 kV.

Scanning electron microscopy (SEM). Samples were dried onto silicon wafers and then mounted on the surface of an aluminum pin stub using double-sided adhesive carbon discs (Agar Scientific). The stubs were then sputter-coated with gold (or palladium) in a high-resolution sputter coater (Agar Scientific, Ltd.) and transferred to a Hitachi 4500 scanning electron microscope.

Matrix assisted laser desorption-ionization time-of-flight mass spectrometry (MALDI-TOF MS). Native and modified TMV particles (10-20 mg in 24 µL water) were denatured by adding 6 µL 6 M guanidine hydrochloride and mixing for 5 min at room temperature. Denatured proteins were spotted onto an MTP 384 massive target plate using mC18 Zip-Tips (Millipore). MALDI-MS analysis was carried out using a Bruker Ultra-Flex I TOF/TOF mass spectrometer.

Particle Testing In Vitro

Cell culture. RAW 264.7 cells (ATCC) were maintained in Dubelco's minimal essential medium (DMEM) at 37° C. in a 5% CO$_2$ humidified atmosphere. The medium was supplemented with 10% (v/v) heat-inactivated fetal bovine serum (FBS), 1% (v/v) L-glutamine, and 1% (v/v) penicillin-streptomycin. All reagents were obtained from Gibco.

Flow cytometry. RAW 264.7 cells (500,000 cells in 200 µL DMEM per well) were added to an untreated 96-well v-bottom plate. The iGd-TMV, Gd-SNP, iGd-TMV-Si, and Gd-SNP-Si particles were added at a concentration of 100,000 particles/cell in triplicate and incubated for 1, 3, and 8 h at 37° C. in a 5% CO$_2$ humidified atmosphere. Following incubation, the cells were pelleted at 500×g for 4 min. The supernatant was removed, and the cells were resuspended in FACS buffer (1 mM EDTA, 1% (v/v) FBS, and 25 mM HEPES, pH 7.0 in Ca$^{2+}$ and Mg$^{2+}$ free PBS). This washing step was carried out three times. The cells were then fixed in 2% (v/v) paraformaldehyde in FACS buffer for 10 min at room temperature and washed another three times. Analysis was carried out using the BD LSR II flow cytometer, and 10,000 events per sample were collected.

Magnetic resonance imaging (MRI) of cell pellets. RAW cells (5×10$^6$ cells in 1 mL DMEM per tube) were added to untreated 1.5 mL Eppendorf tubes. The iGd-TMV, Gd-SNP, iGd-TMV-Si, and Gd-SNP-Si particles were added at a concentration of 1×10$^6$ particles/cell and incubated for 8 h at 37° C. in a 5% CO$_2$ humidified atmosphere. Following incubation, the cells were pelleted at 500×g for 4 min. The supernatant was removed, and the cells were resuspended in FACS buffer. This washing step was carried out three times. The cells were then fixed in 2% (v/v) paraformaldehyde in FACS buffer for 10 min at room temperature and washed another three times. Cells were pelleted in a custom 384 well plate and analysis was carried out using a pre-clinical 7.0 T (300 MHz) MRI (Bruker BioSpec 70/30USR). Following multiple scouting scans, a $T_1$-weighted Multi Slice Multi Echo (MSME) sequence was used with the following parameters: TR/TE=600/8.0 ms, 1 mm thickness, four averages, matrix=128×128, field of view=2.98 cm. Exported DICOM images were analyzed with the free open software OsiriX.

Contrast-to-noise (CNR) calculations. The contrast-to-noise ratio was determined by dividing the mean intensity of the cell pellet area over the mean intensity of the buffer area.

Immunogold labeling. TMV samples were dried on TEM grids, washed with 10 mM sodium phosphate buffer pH 7.0 and floated on a drop of 1% (w/v) bovine serum albumin (BSA) in Tris-buffered saline pH 7.4 plus 0.1% (v/v) Tween-20 (TBST) for 30 min. Samples were equilibrated with 0.1% BSA for 5 min before binding for 1 h with a rabbit anti-TMV antibody (10 μg mL$^{-1}$ in 0.1% BSA). The grids were then washed three times with 0.1% (w/v) BSA before binding with goat anti-rabbit secondary antibodies conjugated to 10-nm gold nanoparticles for 2 h. The grids were then washed in phosphate-buffered saline pH 7.4 plus 0.01% (v/v) Tween-20 (PBST), then water, prior to staining with 2% (v/v) uranyl acetate for 1 min. The grids were imaged by TEM.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, the inventors are not bound by theories described herein. The invention is not limited to the exact details shown and described, for variations obvious to one skilled in the art will be included within the invention defined by the claims.

What is claimed is:

1. An imaging nanoparticle, comprising a tobacco mosaic virus particle having an interior surface and an exterior surface, a chelated lanthanide imaging agent that is linked to the exterior surface, and a layer of silica coated over the exterior surface, wherein the tobacco mosaic virus particle is selected from the group consisting of iGd-TMV-Si, eGd-TMV, eGd-TMV-Si, Gd-SNP, and Gd-SNP-Si, and wherein the tobacco mosaic virus particle has a relaxivity of greater than about 25,000 mM$^{-1}$S$^{-1}$ per particle.

2. The imaging nanoparticle of claim 1, wherein a targeting moiety is linked to the exterior surface of the virus particle.

3. The imaging nanoparticle of claim 2, wherein the targeting moiety binds specifically to an immune cell.

4. The imaging nanoparticle of claim 1, wherein at least about 500 imaging agent molecules are linked to the virus particle.

5. The method of claim 1, wherein the silica maintains the ionic relaxivity of the particles compared to the ionic relaxivity of a non-siliconized particle.

6. The method of claim 1, wherein the silica reduces the immunogenicity of the particles when administered to a subject compared to a non-siliconized particle.

7. A method of generating an image of a tissue region of a subject, by administering to the subject a diagnostically effective amount of an imaging nanoparticle, comprising a tobacco mosaic virus particle having an interior surface and an exterior surface, a chelated lanthanide imaging agent that is linked to the exterior surface, and a layer of silica coated over the exterior surface, wherein the tobacco mosaic virus particle is selected from the group consisting of iGd-TMV-Si, eGd-TMV, eGd-TMV-Si, Gd-SNP, and Gd-SNP-Si, and wherein the tobacco mosaic virus particle has a relaxivity of greater than about 25,000 mM$^{-1}$S$^{-1}$ per particle, and generating an image of the tissue region of the subject to which the imaging nanoparticle has been distributed.

8. The method of claim 7, wherein the method of generating an image is magnetic resonance imaging.

9. The method of claim 7, wherein the imaging nanoparticle further comprises a targeting moiety is linked to the exterior surface of the virus particle.

10. The method of claim 9, wherein the targeting moiety specifically binds to an immune cell.

11. The method of claim 7, wherein the tissue region includes a blood vessel.

12. The method of claim 7, wherein the silica maintains the ionic relaxivity of the particles compared to the ionic relaxivity of a non-mineralized particle.

13. The method of claim 7, wherein the silicon reduces the immunogenicity of the particles when administered to the subject compared to a non-siliconized particle.

* * * * *